(12) United States Patent
Li et al.

(10) Patent No.: US 11,911,764 B2
(45) Date of Patent: Feb. 27, 2024

(54) SYSTEM AND METHOD FOR CELL IMAGING, ANALYSIS AND MEASUREMENT

(71) Applicant: Nexcelom Bioscience LLC, Lawrence, MA (US)

(72) Inventors: Peter Y. Li, Andover, MA (US); Jean Qiu, Andover, MA (US); Leo L. Chan, Lawrence, MA (US); Justin R. Hascup, Lawrence, MA (US); Timothy F. Smith, Lawrence, MA (US); Todd R. Sobolewski, Lawrence, MA (US); Nicholas N. Shaw, Lawrence, MA (US)

(73) Assignee: Nexcelom Bioscience LLC, Lawrence, MA (US)

( * ) Notice: Subject to any disclaimer, the term of this patent is extended or adjusted under 35 U.S.C. 154(b) by 892 days.

(21) Appl. No.: 16/963,233

(22) PCT Filed: Feb. 21, 2019

(86) PCT No.: PCT/US2019/019017
§ 371 (c)(1),
(2) Date: Jul. 19, 2020

(87) PCT Pub. No.: WO2019/165119
PCT Pub. Date: Aug. 29, 2019

(65) Prior Publication Data
US 2021/0069696 A1   Mar. 11, 2021

Related U.S. Application Data

(60) Provisional application No. 62/800,353, filed on Feb. 1, 2019, provisional application No. 62/673,204, filed on May 18, 2018, provisional application No. 62/633,520, filed on Feb. 21, 2018.

(51) Int. Cl.
| C12Q 1/00 | (2006.01) |
| B01L 3/00 | (2006.01) |
| G01N 15/14 | (2006.01) |
| G01N 33/487 | (2006.01) |
| G01N 15/10 | (2006.01) |

(52) U.S. Cl.
CPC .......... B01L 3/5085 (2013.01); G01N 15/147 (2013.01); G01N 33/4875 (2013.01); *B01L 2200/10* (2013.01); *B01L 2300/0654* (2013.01); *B01L 2300/087* (2013.01); *B01L 2300/0829* (2013.01); *G01N 2015/1006* (2013.01); *G01N 2015/1486* (2013.01)

(58) Field of Classification Search
CPC ...................................... B01L 3/5085
See application file for complete search history.

(56) References Cited

U.S. PATENT DOCUMENTS

2013/0114075 A1   5/2013   Hukari et al.
2016/0289623 A1   10/2016   Hung et al.

FOREIGN PATENT DOCUMENTS

WO   2009089189 A2   7/2009
WO   2014058750 A1   4/2014

OTHER PUBLICATIONS

Int'l Search Report and Written Opinon of ISA, PCT/US2019/019017, Apr. 29, 2019.
Extended European Search Report, EP 19756542.7, Oct. 13, 2021.

*Primary Examiner* — Albert M Navarro
(74) *Attorney, Agent, or Firm* — Milstein Zhang & Wu LLC

(57) ABSTRACT

The invention provides novel sample chambers, sample analysis units, multi-well plates, and imaging and analytical systems as well as methods for accurate, efficient and high-throughput imaging, measurement and analysis of diverse types of biological cells to obtain information such as cell count, cell size, cell concentration, cell sub-population, cell morphology, cell viability, etc.

29 Claims, 21 Drawing Sheets

Counted CHO cells in bright field for total cell concentrations

| sample name | count type | cell count | dilution factor | concentration | result type | result | mean diameter | assay type | cell type |
|---|---|---|---|---|---|---|---|---|---|
| 10mL_lmL_plate3_Autofocus | | 12/05/2018 17:12:39 | | | | | | | |
| A1 | BF | 2382 | 1.0 | 2.28e+06 | CHO BF only-DX | CHO BF only-OK | 14.6 | CHO BF only-DX | CHO BF only-OK |

FIG. 8B

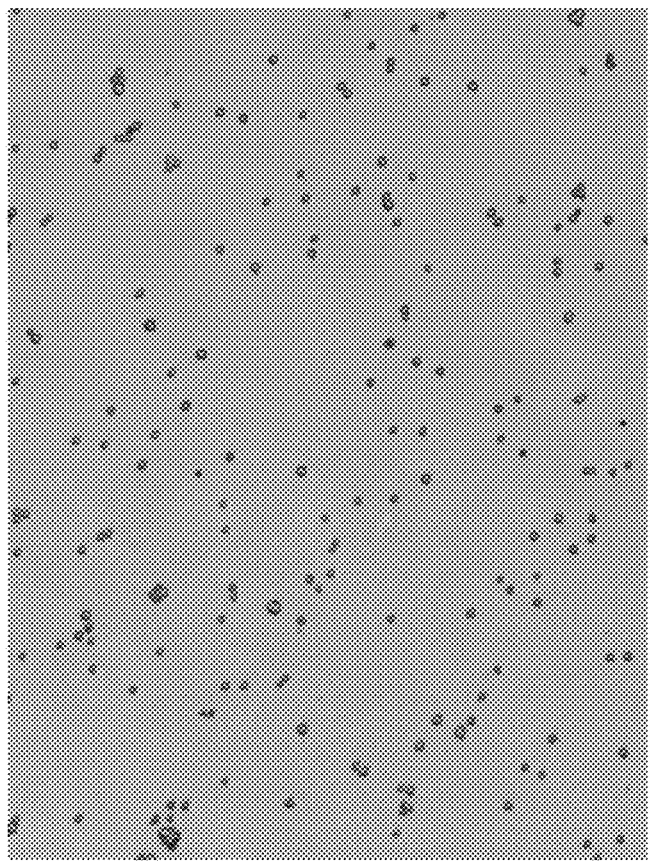
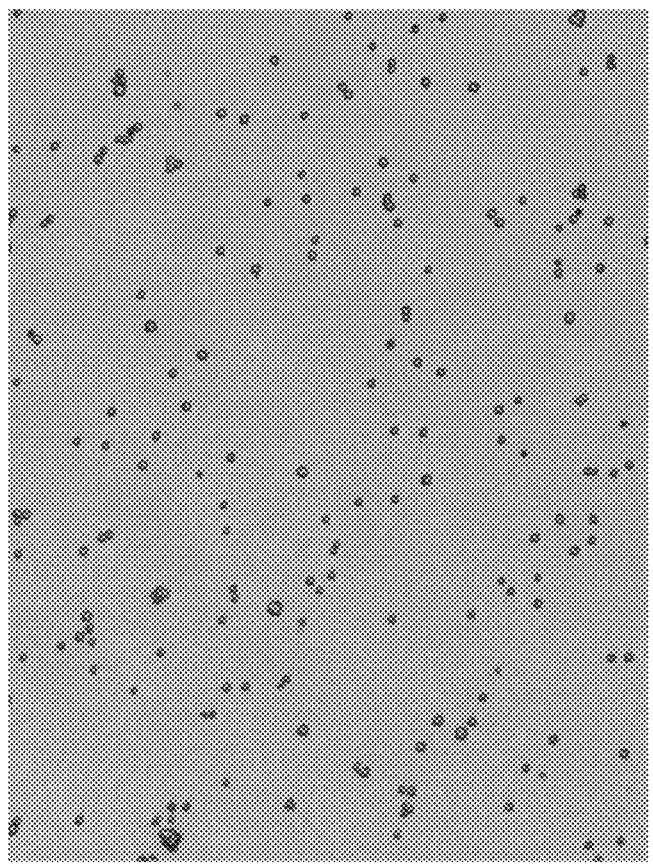
FIG. 9A Counted trypan blue-stained CHO cells in bright field for live and dead cell concentration and viability (a) (b)

| sample name | count type | plate | cell count | dilution factor | concentration | result type | result | mean diameter | assay type | cell type |
|---|---|---|---|---|---|---|---|---|---|---|
| beta testing Laser | | CHO cells | trypan blue2 | 11/13/2018 10:33:44 | | | | | | |
| A1 Live | 1214 | | 2.0 | | 2.34e+06 | Trypan Live | 92.3% | 14.6 | CHO Trypan | CHO Trypan |
| A1 Trypan | 101 | | 2.0 | | 1.95e+05 | Trypan Dead | 7.7% | 10.2 | CHO Trypan | CHO Trypan |
| A1 Total | 1315 | | 2.0 | | 2.54e+06 | Total Cells | | 14.3 | CHO Trypan | CHO Trypan |

FIG. 9B

Counted PBMCs in fluorescence for live cells stained with Acridine Orange and dead cells stained with Propidium Iodide. Live, dead cell concentrations and viability are generated.

FIG. 10B

Counted Jurkat cells in fluorescence for live cells stained with Acridine Orange and dead cells stained with Propidium Iodide. Live, dead cell concentrations and viability are generated.

(a) (b)

| sample name | count type | cell count | dilution factor | concentration | result type | result | mean diameter | assay type | cell type |
|---|---|---|---|---|---|---|---|---|---|
| jurkat 1 | 11/07/2018 | 12:49:48 | | | | | | | |
| A1 F1 | 70 1.0 | 6.71e+04 | | F1/(F1+F2) | 75.4% | 12.8 | jurkat_AOPI | jurkat_AOPI_F1 | |
| A1 F2 | 23 1.0 | 2.19e+04 | | | 11.0 | | jurkat_AOPI | jurkat_AOPI_F2 | |

FIG. 11B

SYSTEM AND METHOD FOR CELL IMAGING, ANALYSIS AND MEASUREMENT

PRIORITY CLAIMS AND RELATED PATENT APPLICATIONS

This application is the U.S. national phase of and claims priority to PCT/US19/19017, filed Feb. 21, 2019, which claims the benefit of priority to U.S. Provisional Application Ser. No. 62/633,520, filed on Feb. 21, 2018; 62/673,204, filed May 18, 2018; and 62/800,353, filed Feb. 1, 2019, the entire content of each of which is incorporated herein by reference for all purposes.

TECHNICAL FIELDS OF THE INVENTION

The invention generally relates to measurement and analysis of biological samples. More particularly, the invention relates to novel sample chambers, sample analysis units, multi-well plates, systems and methods thereof for accurate, efficient and high-throughput imaging, measurement and analysis of diverse types of biological cells, e.g., cell count, cell size, cell concentration, cells sub-population, cell morphology and cell viability measurements.

BACKGROUND OF THE INVENTION

An important aspect in the fields of medical diagnosis and biomedical research involves detection, identification, quantification, and characterization of various cells and biomolecules of interest through testing of biological samples such as blood, spinal fluid, cell culture and urine. Healthcare providers and biomedical researchers routinely analyze such biological samples for the microscopic presence, cell counts and concentrations of cells and biomolecules.

For example, in clinical practice, the concentration of various blood cells, such as red blood cells and white blood cells, can give crucial information regarding the health situation of a patient. Cell counting is an important parameter for perform a cell-based assay. It is used to determine proper seeding density for cell culture, normalization for protein-based assays, or determine number of cells required for downstream assays such as flow cytometry.

Traditionally, cell counting is manually performed with a hemocytometer under a light microscope. In the recent decade, automated cell counters have become available and gained popularity in biology laboratories. These cell counters are mainly for single sample detection and require operator movement to replace disposable slides into the instrument. Although the technology is a significant improvement over manual counting by reducing operation time and operator-dependent variations, it still requires a great amount of time when a large number of samples need to be analyzed.

In cell therapy, for example cell count is used to control the dose of cells administered to a patient. Cell viability measurements, i.e., measuring and calculating the fraction of dead and live cells, can be important in both molecular biology research and in clinical diagnosis. For example, cellular therapy research and development as well as manufacturing typically requires the counting of 10 or more samples from mouse or human. Since counting cells requires 1 to 2 min per sample, it will be approximately 1.5 hours for 50 human peripheral blood mononuclear cell (PBMC) samples. Instruments such as ViCell or Cedex automated the sample preparation step with liquid handling system built into the device. Each sample, however, still requires 2 to 3 min, thus may not provide sufficient time-saving benefit.

Thus, there is an ongoing need for novel and improved methods that allow accurate, efficient and high-throughput imaging, measurement and analysis of diverse biological samples.

SUMMARY OF THE INVENTION

The invention provides distinctively designed sample chambers, sample analysis units, multi-well plates and specially configured cell counting systems suitable for efficient, accurate, and high-throughput measurement of cell counts, concentrations, sub-populations, morphology, viability, cell cycle, surface marker, etc. The multi-well plate is designed to handle samples of diverse cell types and different volumes in automated and accurate capture and analysis of cell images. The invention is especially made for high-throughput cell count and cell-based assays.

In one aspect, the invention generally relates to a sample analysis unit. The sample analysis unit includes: (a) a mixing well for preparation of a liquid sample for analysis; and (b) a sample chamber deposed in spatial proximity to the mixing well without fluid communication therebetween. The sample chamber includes: (i) an inlet for introducing the liquid sample for analysis to the sample chamber; (ii) an imaging well having an imaging chamber for holding the liquid sample for observation or analysis wherein the imaging chamber is in fluid communication with the inlet, an optically transparent window suitable for observation or analysis of the liquid sample inside the imaging chamber, and (iii) an outlet for air escape or outflow of the liquid sample, wherein the outlet is in fluid communication with the imaging chamber. The imaging chamber is characterized by a uniform height traversing at least a portion of the optically transparent window. The mixing well and the sample chamber together form the sample analysis unit.

In another aspect, the invention generally relates to a multi-well plate for sample preparation and analysis. The plate includes: (a) a mixing well for preparation of a liquid sample for analysis; and (b) a sample chamber deposed in spatial proximity to the mixing well without fluid communication therebetween. The sample chamber includes: (i) a first (or inlet) well for introducing the liquid sample for analysis to the sample chamber; (ii) a second (or imaging) well comprising an imaging chamber for holding the liquid sample for observation or analysis; and (iii) a third (or outlet) well for air escape or outflow of the liquid sample. The imaging chamber is in fluid communication with the first (or inlet well) and has an optically transparent window suitable for observation or analysis of the liquid sample inside the imaging chamber. The imaging chamber is characterized by a uniform height traversing at least a portion of the optically transparent window. The third (or outlet) well is in fluid communication with the imaging chamber. The mixing well and the sample chamber together form a unit of the multi-well plate.

In yet another aspect, the invention generally relates to a system for analyzing biological samples, wherein the system includes a multi-well plate disclosed herein.

In yet another aspect, the invention generally relates to a method for preparing and analyzing samples. The method includes: preparing a liquid sample for analysis in the mixing well of a multi-well plate disclosed herein; introducing the prepared liquid sample into the first (or inlet) well of the sample chamber, whereby the liquid sample flows to fill up the image chamber of the second (or image) well and to the third (or outlet) well of the sample chamber; and analyzing the liquid sample via the optically transparent window of the second (or image) well.

In yet another aspect, the invention generally relates to a sample chamber. The sample chamber includes an inlet for introducing the liquid sample for analysis, an imaging well, and an outlet for air escape or outflow of the liquid sample. The imaging well includes an imaging chamber for holding the liquid sample for observation or analysis wherein the imaging chamber is in fluid communication with the inlet; and an optically transparent window suitable for observation or analysis of the liquid sample inside the imaging chamber. The imaging chamber is characterized by a uniform height traversing at least a portion of the optically transparent window. The outlet is in fluid communication with the imaging chamber.

In yet another aspect, the invention generally relates to a sample analysis unit, a multi-well plate, or a device that includes a sample chamber disclosed herein.

In yet another aspect, the invention generally relates to a method for preparing and analyzing samples. The method includes: introducing a liquid sample into an inlet of a sample chamber disclosed herein, whereby the liquid sample flows to fill up the image chamber and to the outlet of the sample chamber; and analyzing the liquid sample via the optically transparent window of the image chamber.

BRIEF DESCRIPTION OF THE DRAWINGS

FIGS. 8A-8B show exemplary images (A) and data (B) of Chinese hamster ovary (CHO) cells obtained with an exemplary system under bright field.

FIGS. 9A-9B show exemplary images (A) and data (B) of live CHO cells and dead CHO cells obtained with an exemplary system under bright field.

FIGS. 10A-10B show exemplary images (A) and data (B) of live and dead peripheral blood mononuclear cells (PBMCs) obtained with an exemplary system under bright field and green/red fluorescence.

FIGS. 11A-11B show exemplary images (A) and data (B) of live and dead Jurkat cells obtained with an exemplary system under bright field and green/red fluorescence.

DETAILED DESCRIPTION OF THE INVENTION

The invention features uniquely designed sample chambers, sample analysis units, multi-well plates and cell counting systems suitable for efficient, accurate, and high-throughput measurement of cell counts, concentrations, subpopulations, morphology, viability, cell cycle, surface marker, etc. A key feature of the present invention is the multi-well plate's ability to handle samples of diverse cell types and different volumes and automatically and accurately capture and analyze cell images.

Another key feature of the invention is a system and method that enables high-throughput cell count and cell-based assays. For example, according to an embodiment of the invention, a 96-well plate is able to perform automated cell counting and analysis on 24 samples simultaneously.

Figure 1:
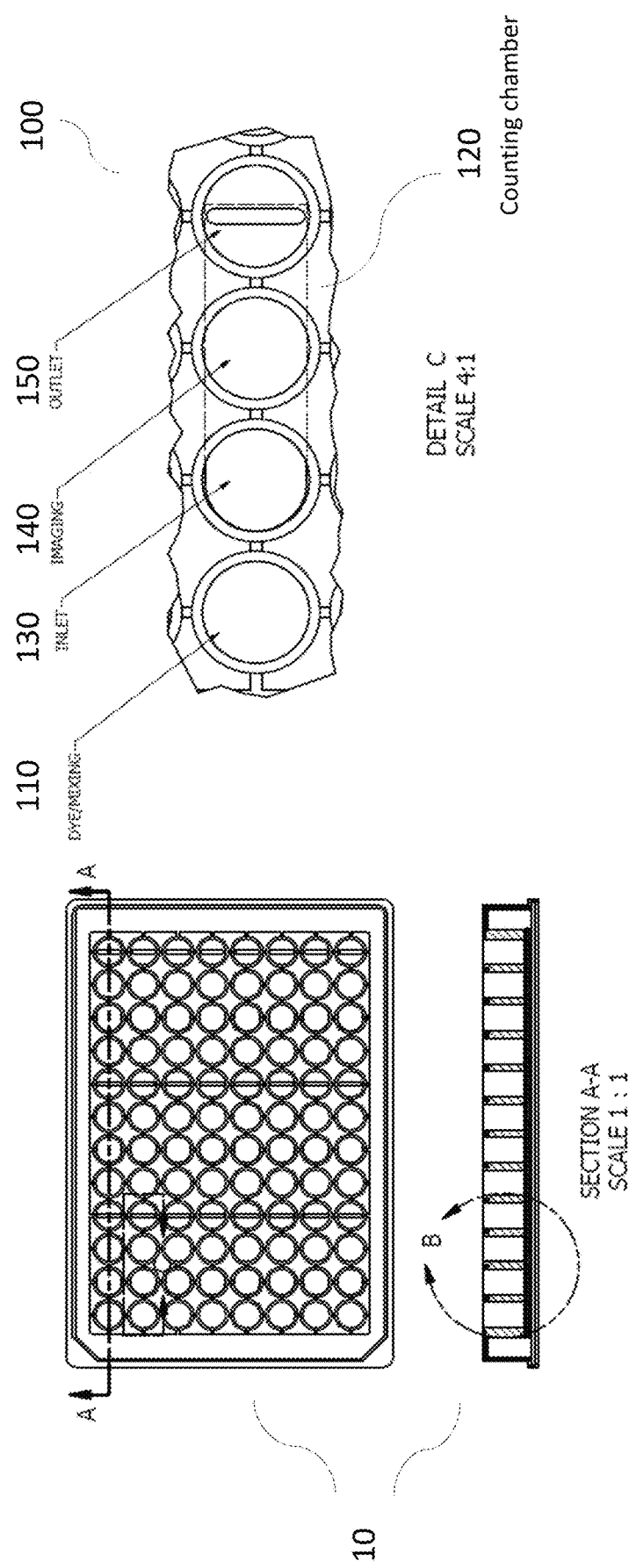
FIG. 1 illustrates an exemplary cell counting plate according to an embodiment of the invention.

FIG. 1 illustrates an exemplary cell counting plate 10 of the invention that is comprised of 24 groups of four-well units, totaling 96 wells. As shown in FIG. 1, each unit 100 has four wells, including a mixing well 110 for mixing cells and staining agents (including dyes or labels) and a counting chamber 120, which is comprised of an inlet well (or introductory port) 130 for introducing a sample, an imaging well 140 having a cell imaging chamber, and an outlet well (or an air escape port) 150.

Figure 2A:
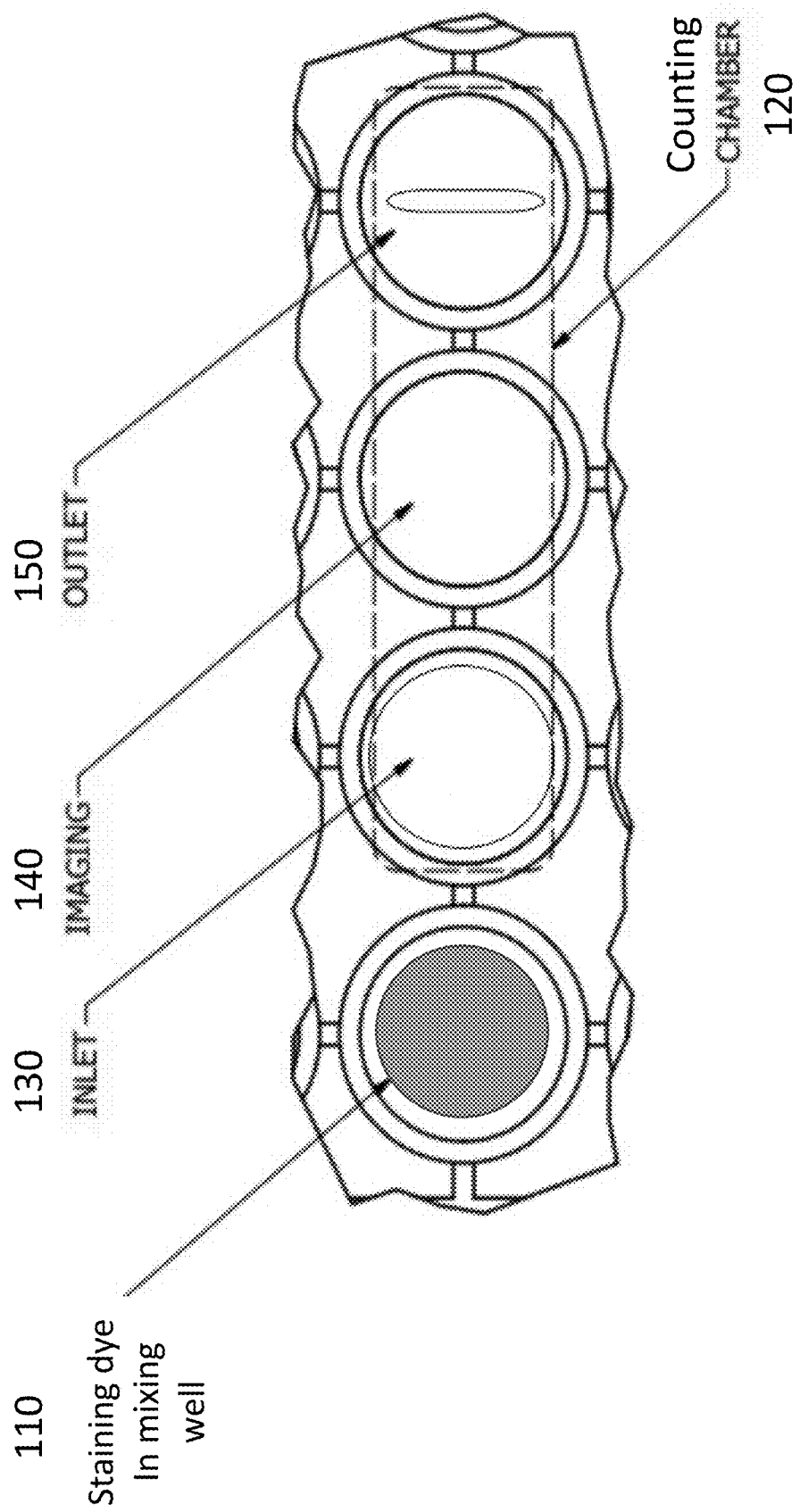
FIGS. 2A-2B illustrate an embodiment of the mixing well with a staining agent (including dyes or labels) (in dry form) prior to addition of and mixing with cells.
Figure 2B:
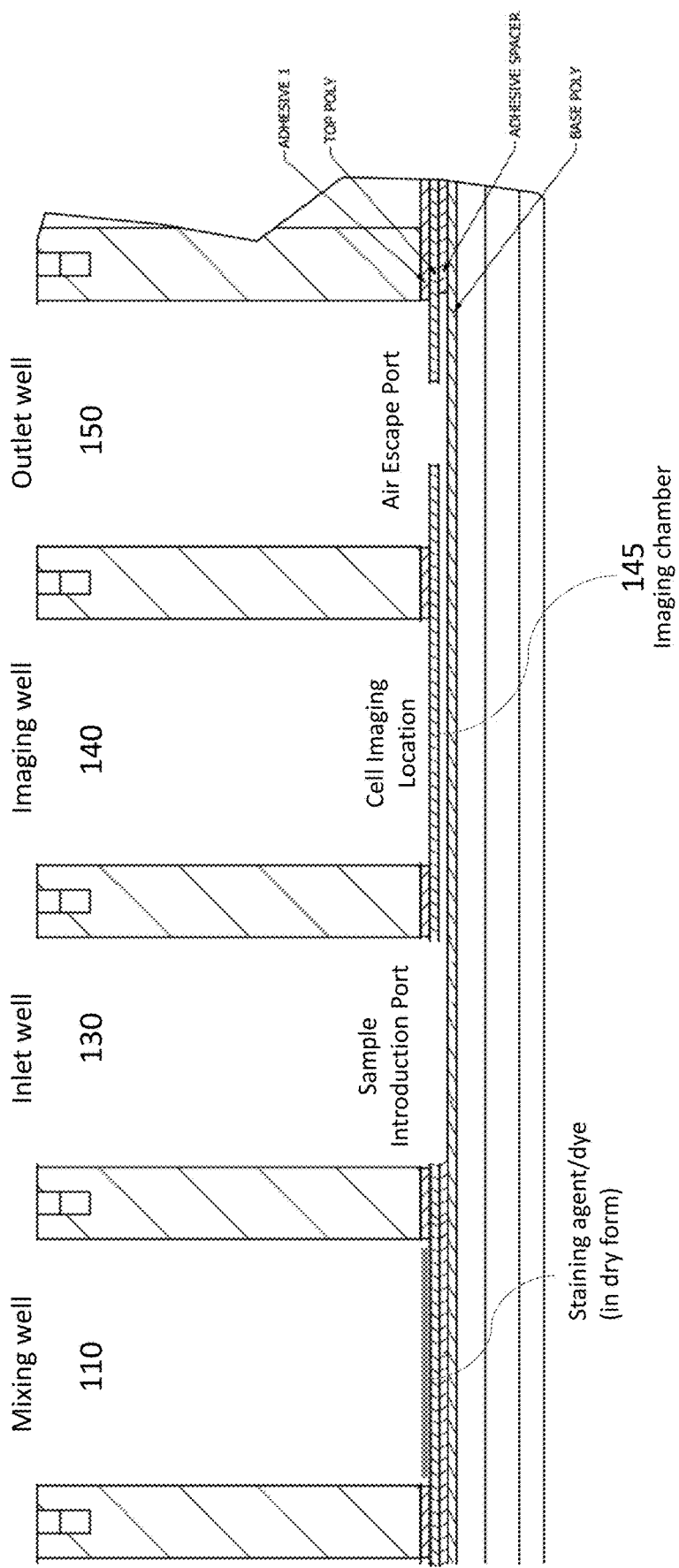

Together, the illustrated exemplary plate 10 has a total of 24 mixing wells and 24 counting chambers allowing 24 samples to be analyzed and measured simultaneously. The cell and staining agent mixing wells 110 allow mixing of cells and stains prior to introducing the samples to the counting chambers 120 via inlet wells 130. FIG. 2A and FIG. 2B show the mixing well with a staining agent (in dry form) prior to addition of and mixing with cells. After the cells and staining agents are mixed, the samples are transferred by a pipette (e.g., a single channel or multi-channel pipette) or liquid handler into the respective inlet wells 130.

Figure 3A:
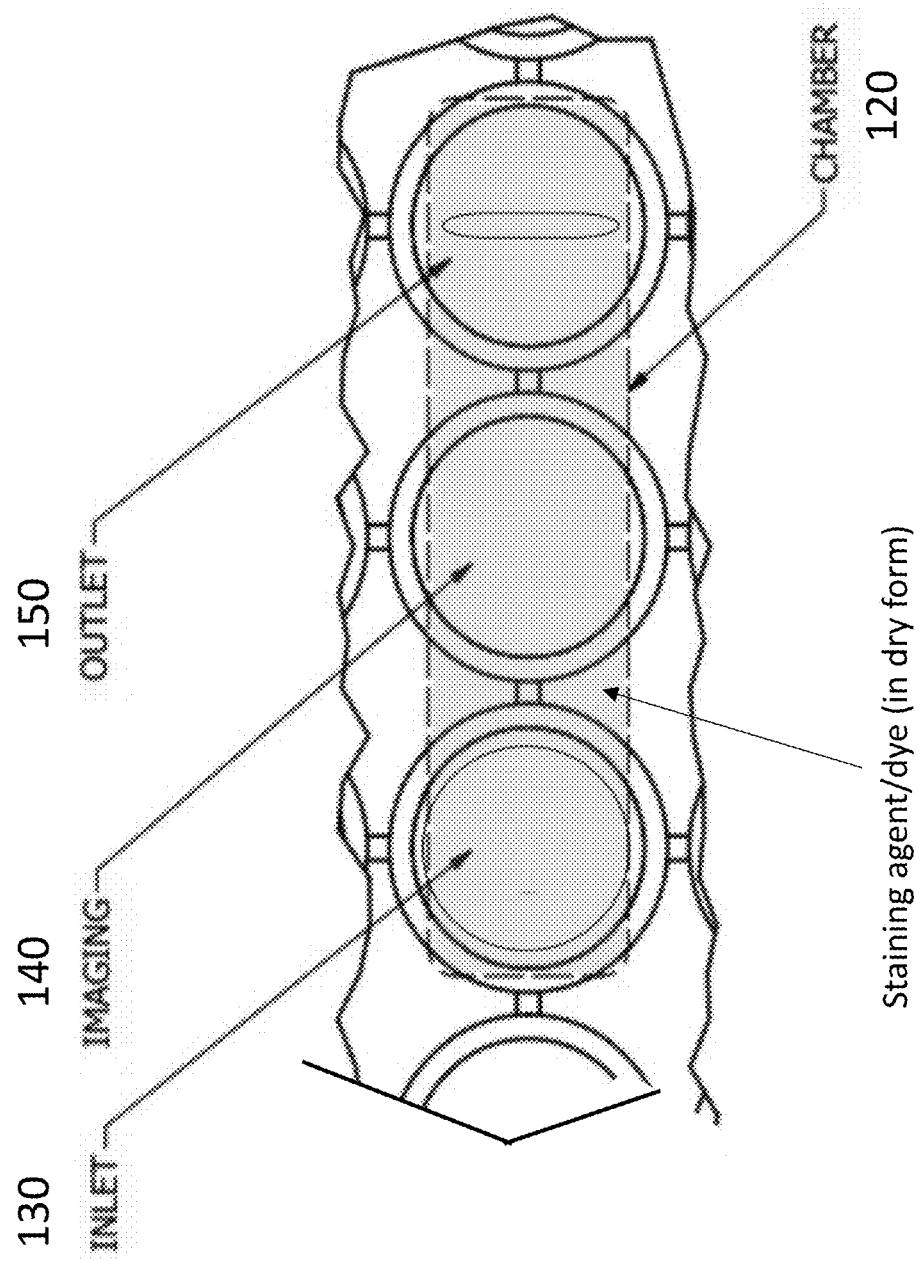
FIGS. 3A-3B illustrate an exemplary counting chamber filled with a sample, wherein the sample occupies the inlet well, the imaging chamber and the outlet well.
Figure 3B:
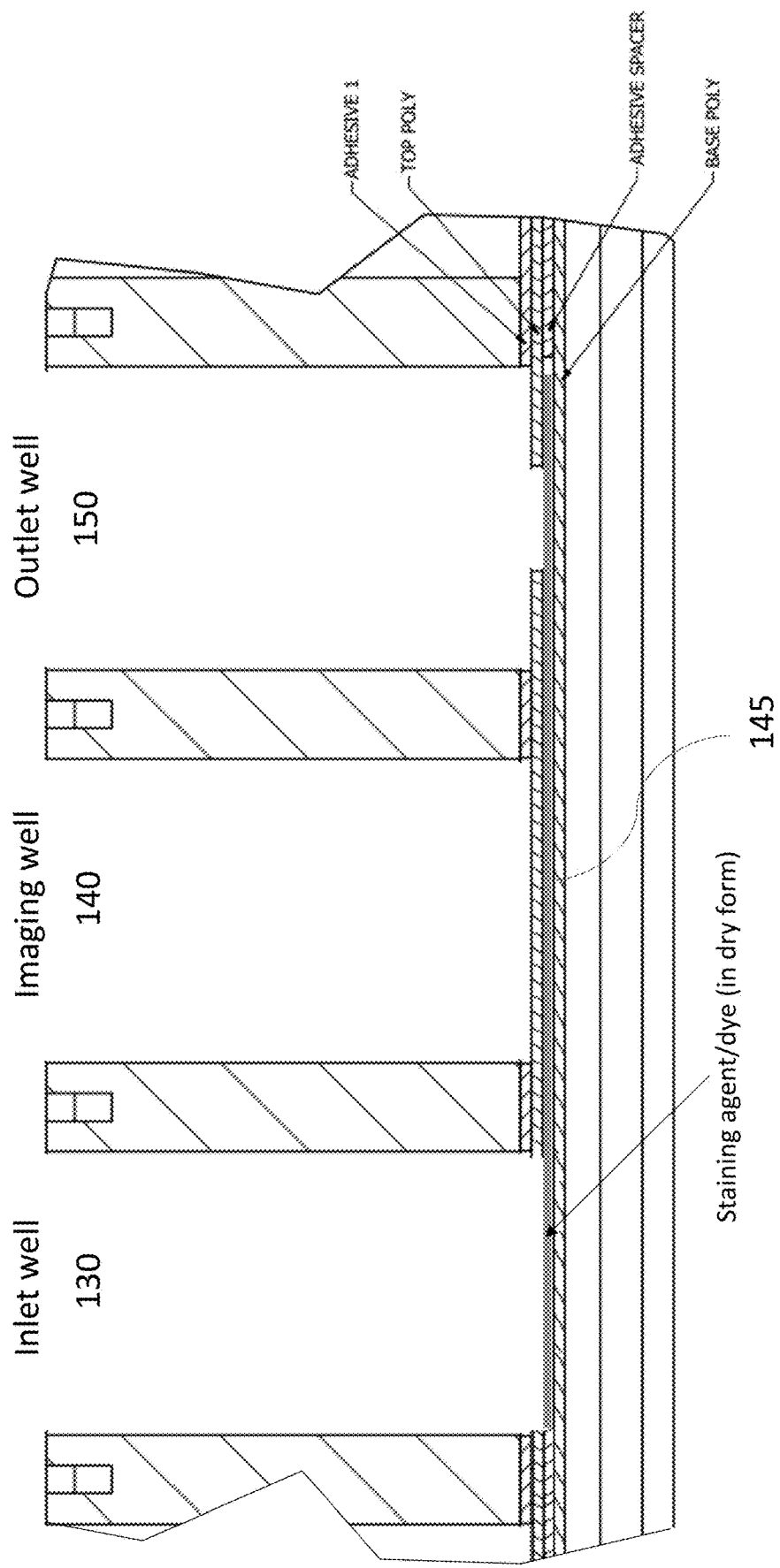

FIG. 3A and FIG. 3B depict a counting chamber 120 filled with the sample, wherein the sample occupies the inlet well 130, the imaging chamber 145 and the outlet well 150. The air in the chamber exits the imaging chamber 145 via the outlet well 150. The cells are allowed to settle in the imaging chamber 145 where observation, imaging and/or measurements can take place. For instance, the cell sample may be allowed to form a monolayer in the imaging chamber 145 where they can be visualized by microscope, imaged or analyzed using bright field, blue, green, red, and far red fluorescence.

Figure 4A:
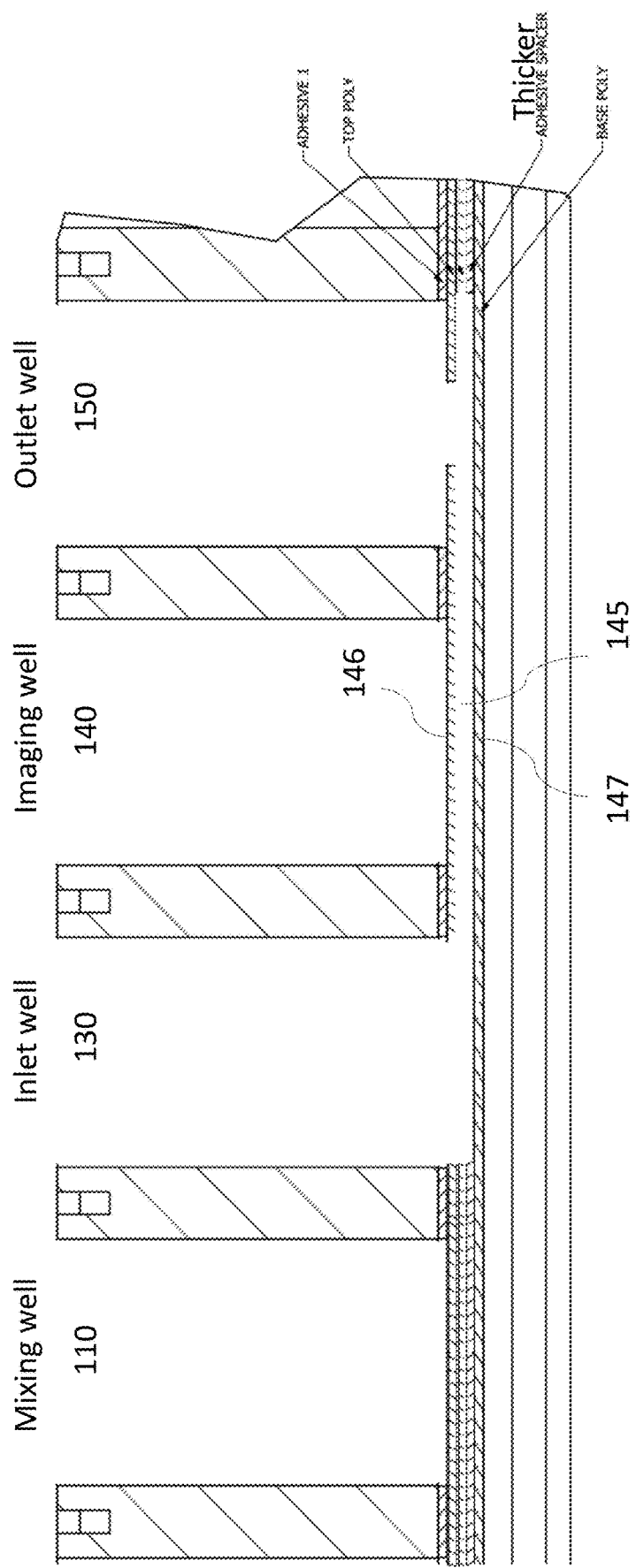
FIGS. 4A-4B illustrate an exemplary imaging chamber having a uniform (A) or non-uniform (B) depth (or height) defined by the distance between a top wall (ceiling) and a bottom wall (floor).
Figure 4B:
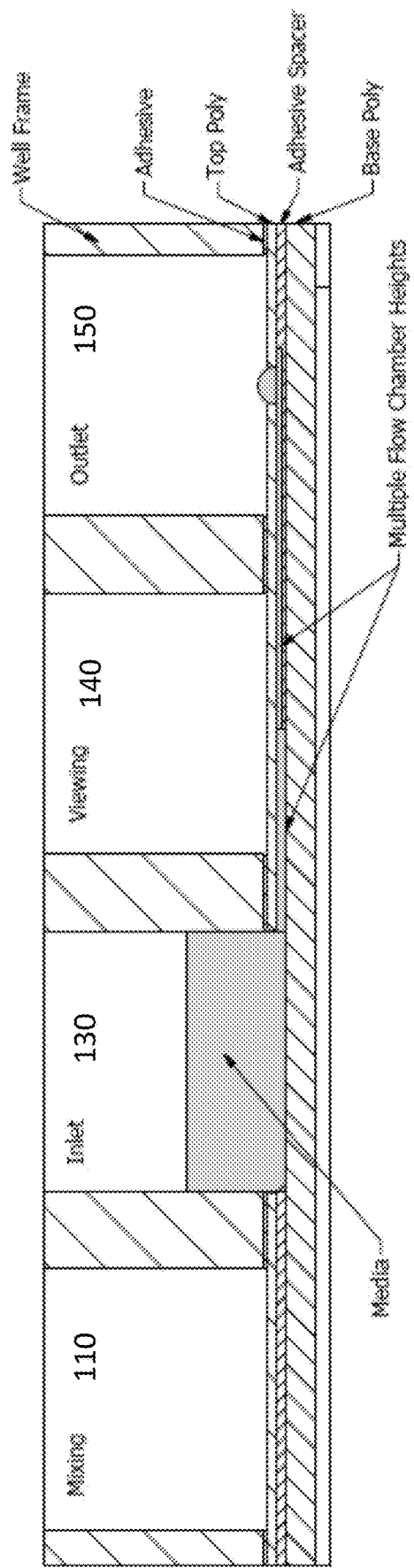

As illustrated in FIG. 4A, the imaging chamber 145 typically has a uniform depth (or height) defined by the distance between a top wall (ceiling) 146 and a bottom wall (floor) 147. The depth of the imaging chamber 145 can be controlled during fabrication to have any suitable value, for example, less than 20 μm for bacteria, yeast or platelets and up to 1 mm for spheroids and islet cells. It is noted that the imaging chamber 145 may be configured to have two or more sections or compartments with different depth (or height), as is illustrated in FIG. 4B.

Figure 5A:
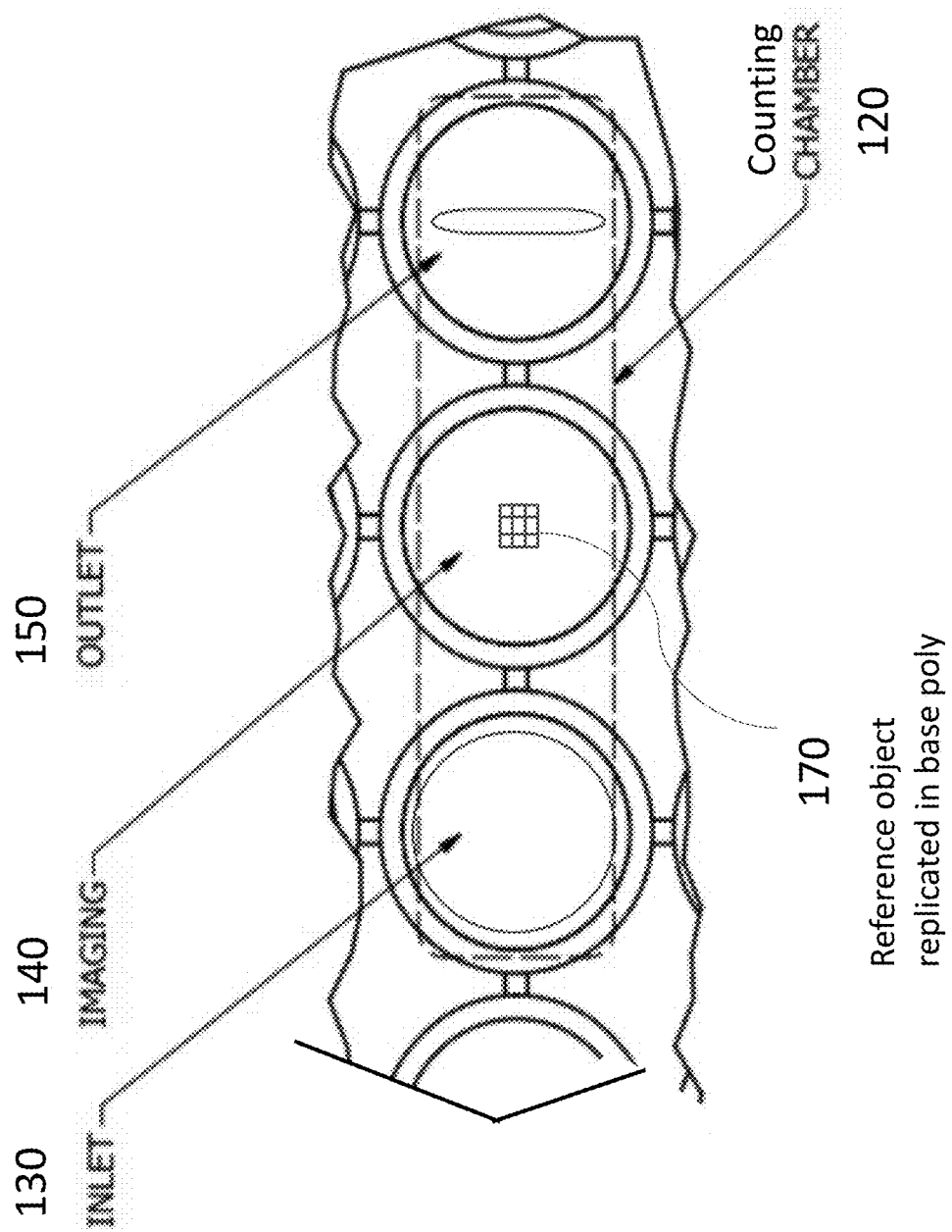
FIGS. 5A-5B illustrate an exemplary imaging chamber having reference markings on the bottom wall (floor) of the imaging chamber.
Figure 5B:
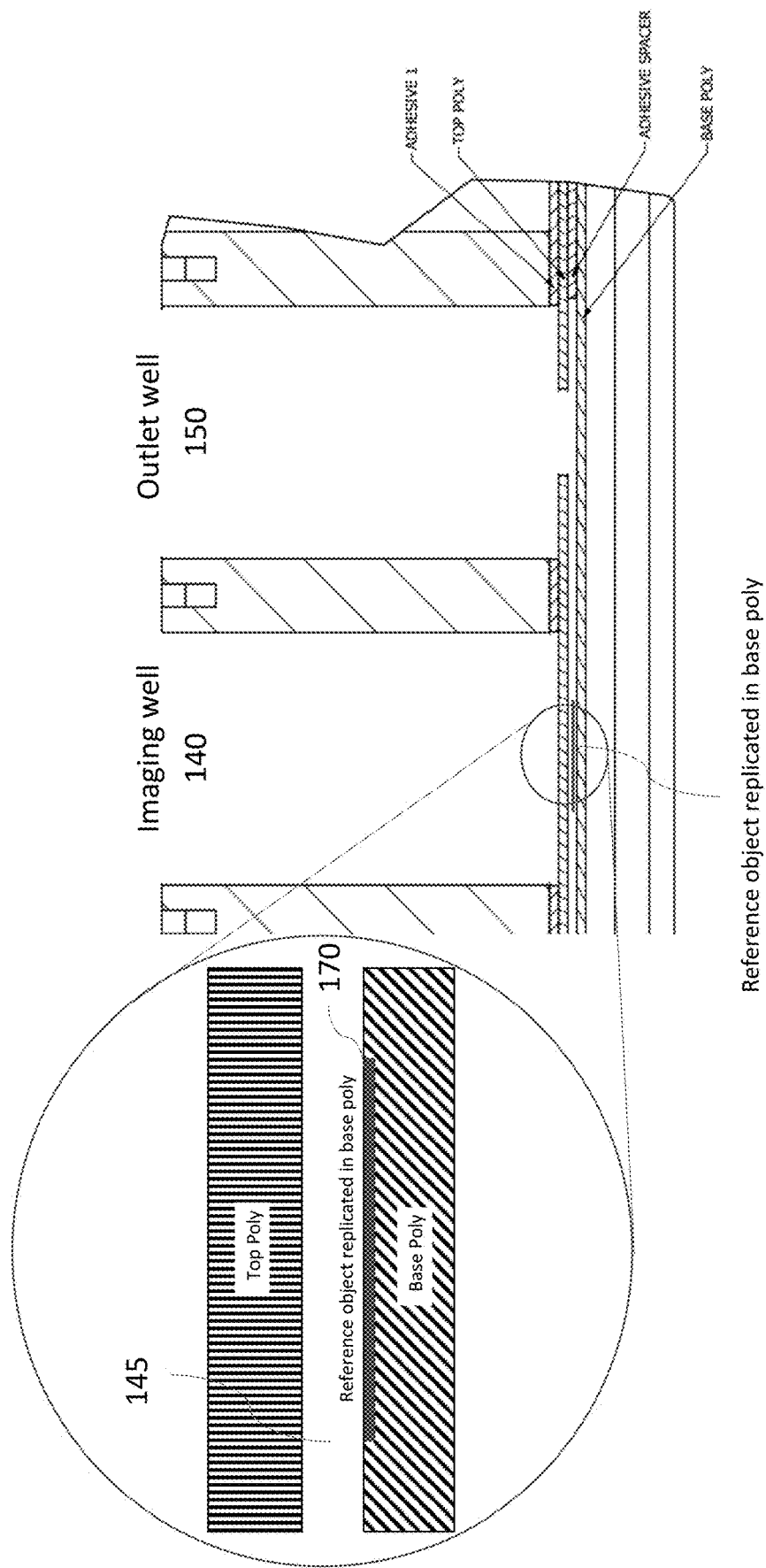

As depicted in FIG. 5A and FIG. 5B, a reference object 170 such as a counting grid, location or autofocus markings may be provided on the top wall (ceiling) and/or bottom wall (floor) walls of the imaging chamber 145.

Figure 6A:
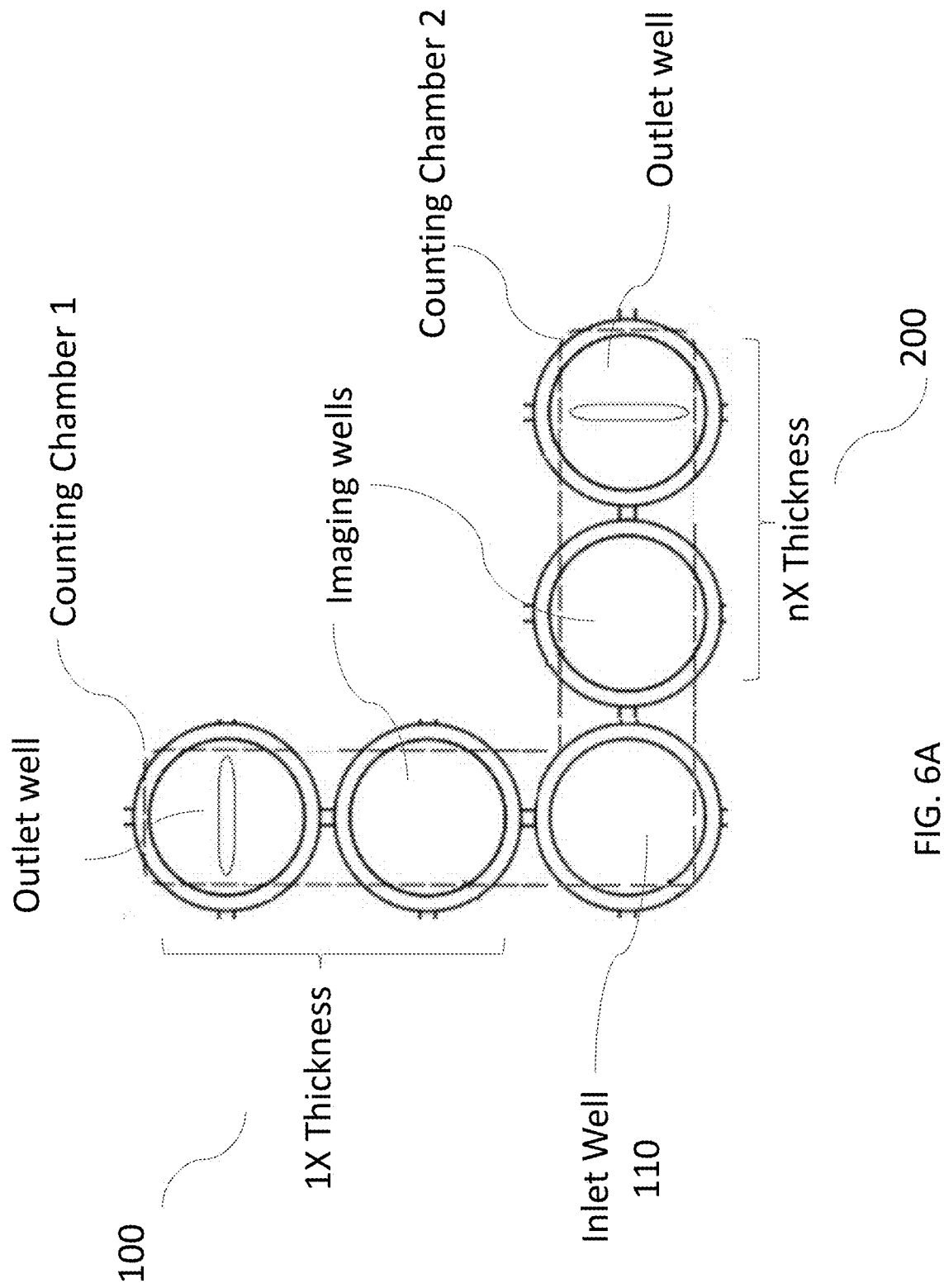
FIGS. 6A-6B illustrate exemplary cell counting plate units wherein two (A) or four (B) units share a common mixing well.
Figure 6B:
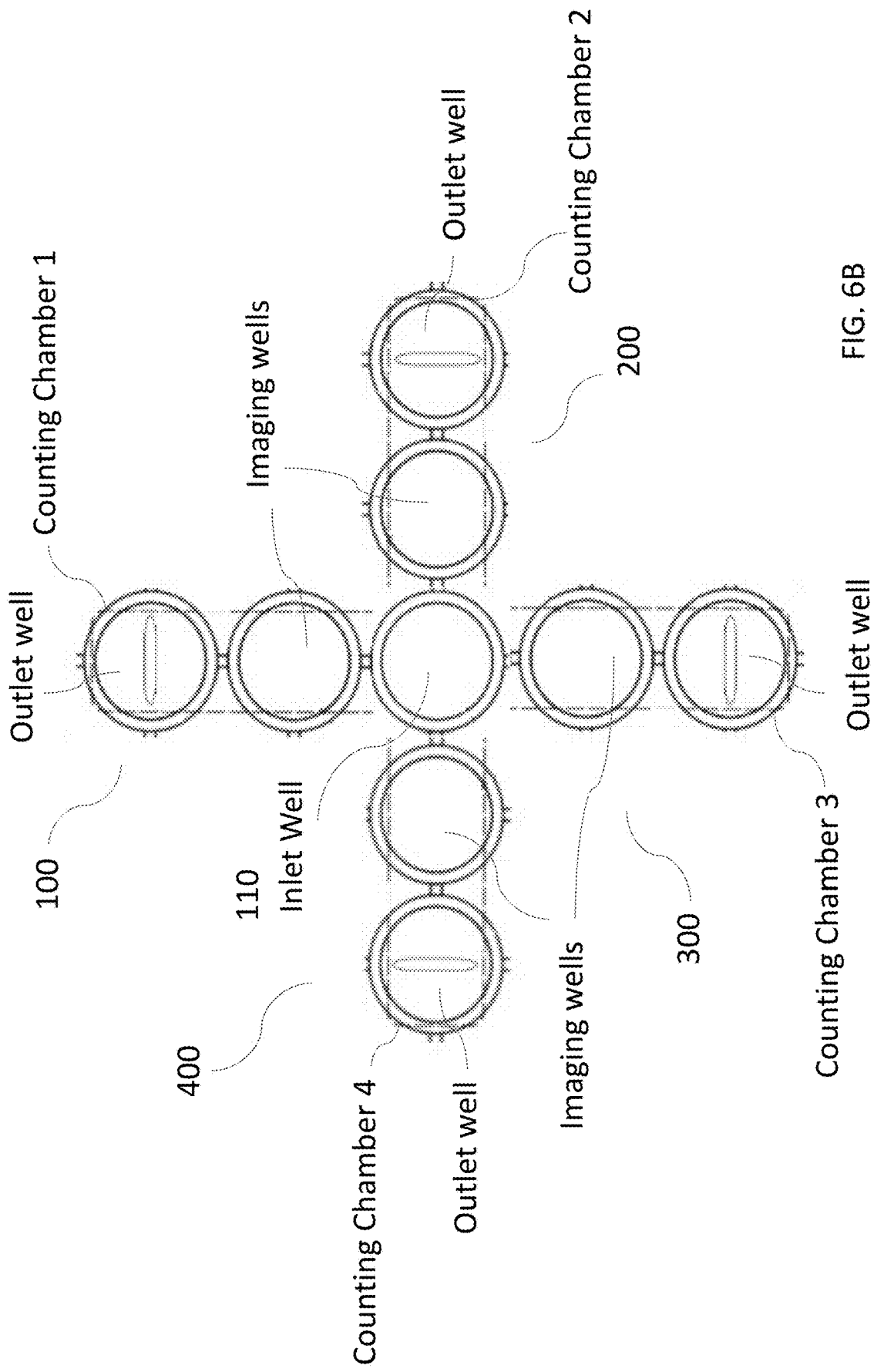

In another embodiment, as illustrated in FIG. 6A, two units 100 and 200 share a common mixing well 110. The number of units that share a common mixing well may be any suitable number, for example, 3 or 4. FIG. 6B depicts the later configuration whether a common mixing well 110 is shared among four units (i.e., one mixing well is deposed with four counting chambers). Each of the counting chambers may have the same or different depth.

In certain embodiments, the unit 100 may further include a sample storage well 180 and/or an additional mixing well 190.

An important feature of the invention is that a wide range of sample volume can be accommodated without affecting measurement accuracy. The cell counting plate allows accurate cell concentration measurements and other analysis independent of the volume a user pipettes into the sample inlet well, which allows greater flexibility in sample preparation and handling. For example, by pipetting any amount between 50 µL and 200 µL of cell sample, the resultant measurement remains consistent (i.e., not impacted by the actual volume of sample used).

Figure 7A:
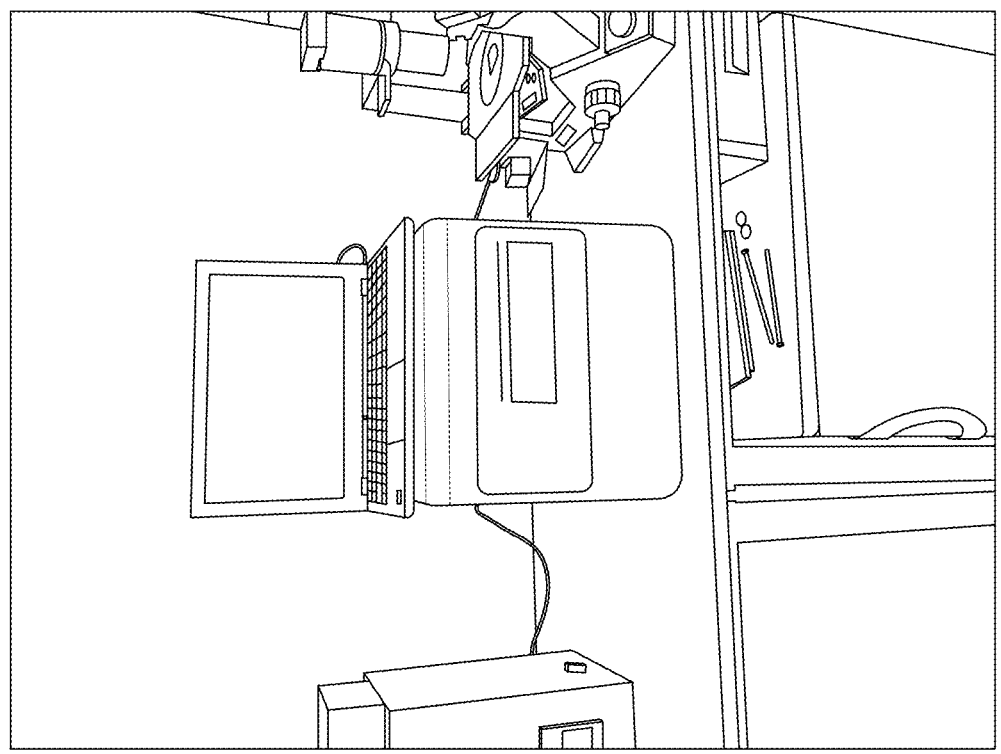
FIGS. 7A-7B show an exemplary system (A) that embodies certain aspects of the invention with certain components illustrated in (B).
Figure 7B:
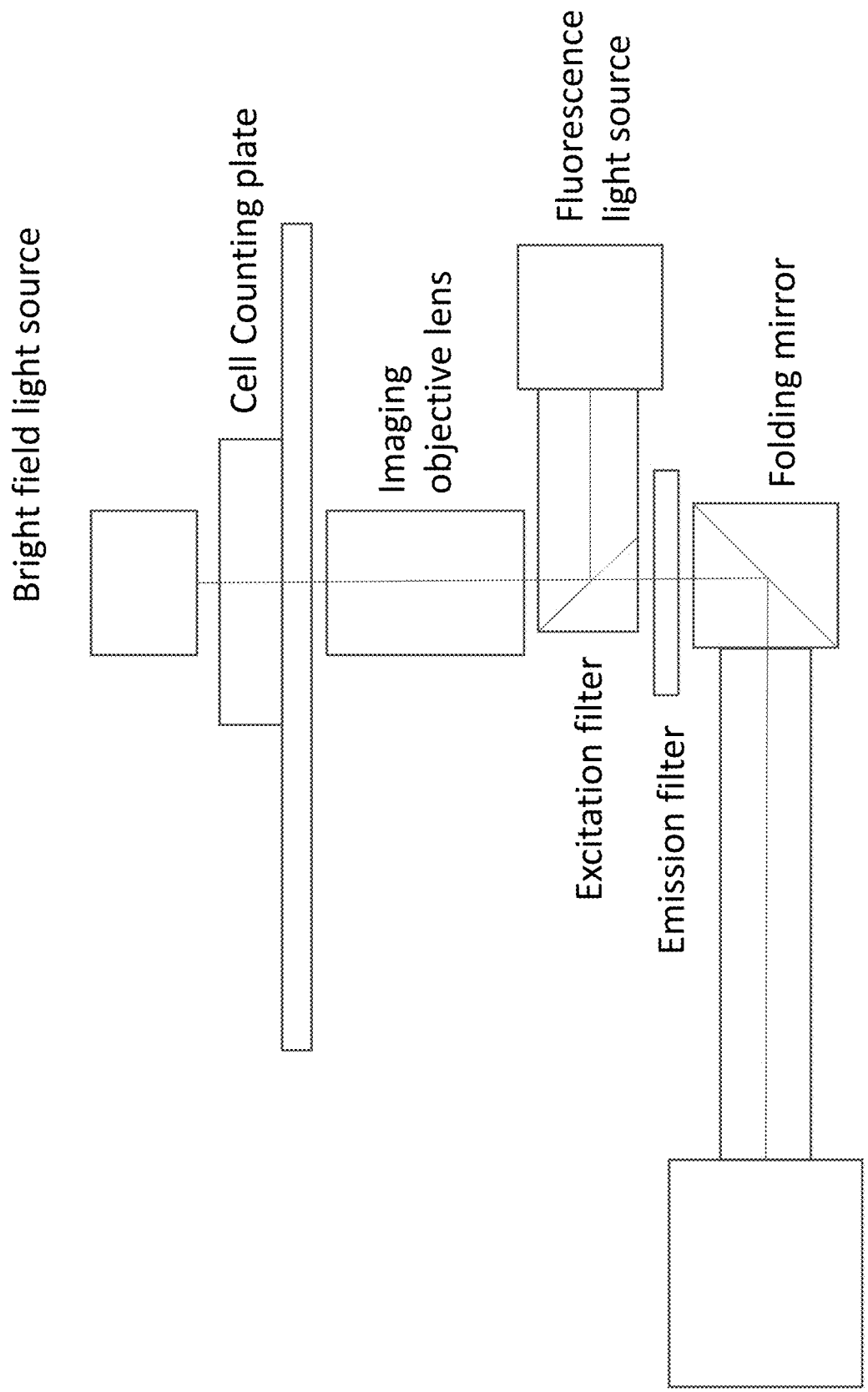

An important feature of the invention is a high-throughput cell counter instrumentation and associated software. An example of such a system is depicted in FIG. 7A. As depicted in FIG. 7B, the exemplary system utilizes a transmission bright field channel, five excitation filters (375, 475, 530, 540, 630 nm) and six emission filters (450, 525, 600, 610LP, 660, 695) for epi-fluorescent channels. It also uses infinity-corrected optical objectives for high-resolution high-quality imaging. The exemplary system allows X-Y-Z motion to image and analyze cells in standard microplates (6-1536 wells), T25 and T75 flasks, as well as glass and chamber slides. It improves cell counting time to 24 samples/min for bright field analysis (trypan blue) and 24 samples/3 min for fluorescence analysis (acridine orange and propidium iodide).

In addition, the instrument can be integrated with liquid handler to perform fully automated high-throughput cell counting process.

The exemplary system is built with software that is designed to image and analyze different consumable type such as cell counting plate disclosed herein, standard microplates from 6-1536-well, glass slides, T75, T25 flasks, chamber slides. It may be utilized to measure cell concentration, cell size and morphology such as perimeter, circularity, area, major/minor axis, compactness, elongation, eccentricity, sphericity, convexity, aspect ratio, solidity. It can measure fluorescent intensities for fluorescence-based assays. Additional add-on is for full automation to integrate with plate handler, liquid handler for high-throughput cell counting and analysis.

The software analyzes the captured images to determine cell concentrations, cell size and morphology, fluorescently labeled population percentages such as labels for viability (Acridine Orange, Propidium Iodide (PI), 4',6-diamidino-2-phenylindole (DAPI), Hoechst, 7-Aminoactinomycin D (7AAD), Sytox Green, Sytox Red, DRAQ5/7, nuclear green/red/blue/far red, trypan blue, etc.); transduction efficiency (green fluorescent protein (GFP), red fluorescent protein (RFP), mCherry, blue fluorescent protein (BFP), mCardinal, yellow fluorescent protein (YFP), Cyan fluorescent protein (CFP), etc.); apoptosis (Annexin V-FITC, -PE and PI, or Caspase 3/7); autophagy (LC3II-FITC, -GFP); cell cycle (PI, Hoechst, DAPI, BrdU (bromodeoxyuridine), EdU (5-ethynyl-2'-deoxyuridine)); senescence (Beta-Gal-Green); vitality (Calcein AM, CFDA-AM (5-Carboxyfluorescein diacetate acetoxymethyl ester), FDA (Fluorescein diacetate), CFDA); ROS; mitochondrial Potential and health; surface marker staining and intracellular staining.

A system according to the invention can be designed to perform assays for oncology, immuno-oncology, virology, cell therapy, cell line development, regenerative medicine (stem cell research), brewing science and renewable energy. It may be utilized to analyze cell lines (NCI-60 cancer cells and other), primary cells (PBMCs, splenocytes, leukapheresis, apheresis, thymocytes), stem cells, platelets, red blood cells, yeast, and algae, CHO cells, etc. The system can be used to perform assays such as cell growth and proliferation, viability, cell size change by activation, transduction efficiency, apoptosis, autophagy, cell cycle, senescence, ROS, mitochondrial potential and health, surface marker population analysis, intracellular staining population analysis, etc.

In addition, the system can determine population percentages based on size, morphology, or fluorescent labeling. By identifying total cell count with bright field or any other fluorescent channels, the ratio of the population can be determined by comparing the number of cell count or concentration of target cell population based on size, morphology, or fluorescent labeling.

In one aspect, the invention generally relates to a sample analysis unit. The sample analysis unit includes: (a) a mixing well for preparation of a liquid sample for analysis; and (b) a sample chamber deposed in spatial proximity to the mixing well without fluid communication therebetween. The sample chamber includes: (i) an inlet for introducing the liquid sample for analysis to the sample chamber; (ii) an imaging well having an imaging chamber for holding the liquid sample for observation or analysis wherein the imaging chamber is in fluid communication with the inlet, an optically transparent window suitable for observation or analysis of the liquid sample inside the imaging chamber, and (iii) an outlet for air escape or outflow of the liquid sample, wherein the outlet is in fluid communication with the imaging chamber. The imaging chamber is characterized by a uniform height traversing at least a portion of the optically transparent window. The mixing well and the sample chamber together form the sample analysis unit.

In certain embodiments, the sample chamber includes: (ii) two or more imaging wells, each of which having an imaging chamber for holding the liquid sample for observation or analysis wherein said imaging chamber is in fluid communication with the inlet, an optically transparent window suitable for observation or analysis of the liquid sample inside said imaging chamber, and two or more of corresponding outlets for air escape or outflow of the liquid sample, each being in fluid communication with a corresponding imaging chamber. The imaging chamber is characterized by a uniform height traversing at least a portion of the optically transparent window.

In certain embodiments, the sample chamber comprises one inlet, two imaging wells, and two outlets. In certain embodiments, the sample chamber comprises one inlet, four imaging wells, and four outlets.

In certain embodiments of the sample analysis unit, the mixing well is configured to have a volume of about 1 µL to about 500 µL (e.g., about 1 µL to about 300 µL, about 1 µL to about 200 µL, about 1 µL to about 100 µL, about 1 µL to about 50 µL, about 1 µL to about 20 µL, about 1 µL to about 10 µL, about 10 µL to about 500 µL, about 50 µL to about 500 µL, about 100 µL to about 500 µL, about 10 µL to about 50 µL, about 50 µL to about 100 µL, about 20 µL to about 100 µL, about 50 µL to about 200 µL).

In certain embodiments of the sample analysis unit, the sample chamber is configured to have a volume of about 1 µL to about 500 µL (e.g., about 1 µL to about 300 µL, about 1 µL to about 200 µL, about 1 µL to about 100 µL, about 1 µL to about 50 µL, about 1 µL to about 20 µL, about 1 µL to about 10 µL, about 10 µL to about 500 µL, about 50 µL to about 500 µL, about 100 µL to about 500 µL, about 10 µL to about 50 µL, about 50 µL to about 100 µL, about 20 µL to about 100 µL, about 50 µL to about 200 µL).

In certain embodiments of the sample analysis unit, the imaging chamber is configured to have a volume of about 0.2 µL to about 10 µL (e.g., about 0.2 µL to about 5 µL, about 0.2 µL to about 2 µL, about 0.2 µL to about 1 µL, about 0.2 µL to about 0.5 µL, about 0.5 µL to about 10 µL, about 1 µL to about 10 µL, about 2 µL to about 10 µL, about 5 µL to about 10 µL, about 0.5 µL to about 2 µL, about 2 µL to about 5 µL).

In certain embodiments of the sample analysis unit, the imaging chamber has a top wall (ceiling) and a bottom wall (floor) with a uniform height (or depth) therebetween.

In certain embodiments of the sample analysis unit, the imaging chamber has a top wall (ceiling) and a bottom wall (floor) with a non-uniform height (or depth) therebetween.

In certain embodiments of the sample analysis unit, the imaging chamber comprises a first portion of the top wall (ceiling) and a first portion of the bottom wall (floor) providing a first height (or depth) therebetween and a second portion of the top wall and a second portion of the bottom wall (floor) providing a second height (or depth) therebetween.

The height(s) of the imaging chamber in the sample analysis unit can be any suitable value, for example, in the range from about 1 µm to about 1 mm (e.g., about 1 µm to about 0.5 mm, about 1 µm to about 0.1 mm, about 1 µm to about 50 µm, about 1 µm to about 20 µm, about 1 µm to about 10 µm, about 5 µm to about 1 mm, about 10 µm to about 1 mm, about 0.1 mm to about 1 mm, about 0.5 mm to about 1 mm, about 2 µm to about 10 µm, about 10 µm to about 0.1 mm).

In certain embodiments, the height(s) is in the range from about 1 µm to about 20 µm (e.g., about 1 µm to about 5 µm, about 5 µm to about 10 µm, about 10 µm to about 15 µm, about 15 µm to about 20 µm). In certain embodiments, the height(s) is in the range from about 20 µm to about 1 mm (e.g., about 20 µm to about 0.1 mm, about 0.1 mm to about 0.5 mm, about 0.5 mm to about 1 mm).

In certain embodiments of the imaging chamber in the sample analysis unit, the top wall (ceiling) and/or the bottom wall (floor) has one or more markings, e.g., as a counting grid, for reference or for autofocusing.

In certain embodiments of the sample analysis unit, the one or more markings on the imaging chamber has unit markings ranging from about 0.1 µm to about 1 mm (e.g., about 0.1 µm to about 1 mm, about 1 µm to about 1 mm, about 10 µm to about 1 mm, about 0.1 mm to about 1 mm, about 0.1 µm to about 0.1 mm, about 0.1 µm to about 10 µm, about 0.1 µm to about 1 µm, about 1 µm to about 10 µm, about 1 µm to about 25 µm, about 10 µm to about 0.1 mm). In certain embodiments, the one or more markings has unit markings ranging from about 1 µm to about 25 µm (e.g., about 1 µm to about 5 µm, about 5 µm to about 10 µm, about 10 µm to about 25 µm).

In certain embodiments of the sample analysis unit, the first (or inlet) well is open to ambient atmosphere (e.g., ambient pressure) during operation.

In certain embodiments of the sample analysis unit, the first (or inlet) well is closed to ambient atmosphere (e.g., ambient pressure) during operation.

In certain embodiments of the sample analysis unit, the third (or outlet) well is open to ambient atmosphere (e.g., ambient pressure) during operation.

In certain embodiments of the sample analysis unit, the third (or outlet) well is closed to ambient atmosphere (e.g., ambient pressure) during operation.

In certain embodiments of the sample analysis unit, the mixing well has on its bottom a staining agent in dry form.

In another aspect, the invention generally relates to a multi-well plate for sample preparation and analysis. The plate includes: (a) a mixing well for preparation of a liquid sample for analysis; and (b) a sample chamber deposed in spatial proximity to the mixing well without fluid communication therebetween. The sample chamber includes: (i) a first (or inlet) well for introducing the liquid sample for analysis to the sample chamber; (ii) a second (or imaging) well comprising an imaging chamber for holding the liquid sample for observation or analysis; and (iii) a third (or outlet) well for air escape or outflow of the liquid sample. The imaging chamber is in fluid communication with the first (or inlet well) and has an optically transparent window suitable for observation or analysis of the liquid sample inside the imaging chamber. The imaging chamber is characterized by a uniform height traversing at least a portion of the optically transparent window. The third (or outlet) well is in fluid communication with the imaging chamber. The mixing well and the sample chamber together form a unit of the multi-well plate.

In certain embodiments, the multi-well plate is comprised of 2 or more (e.g., 4, 8, 16, 32, 64, 96, or more) of the multi-well units. In certain embodiments, the multi-well plate is comprised of 96 or more (e.g., 192, 384, or more) of the multi-well units. In certain embodiments, the multi-well plate is comprised of 384 or more of the multi-well units.

It is noted that the sample analysis unit having a mixing well, a sample inlet, an imaging area, and an air/fluid outlet, an aspect of the invention, can be fabricated on various substrates such as Society for Biomolecular Screening (SBS) plates, plastic or glass substrate.

In certain embodiments of the multi-well plate, the sample chamber further includes: two or more of second (or imaging) wells and two or more of corresponding third (or outlet) wells for air escape or outflow of the liquid sample. Each second (or imaging) well includes an imaging chamber for holding the liquid sample for observation or analysis wherein said imaging chamber is in fluid communication with the first (or inlet well). Each second (or imaging) well also includes an optically transparent window suitable for observation or analysis of the liquid sample inside said imaging chamber. The imaging chamber is characterized by a uniform height traversing at least a portion of the optically transparent window. Each third (or outlet) well is in fluid communication with a corresponding imaging chamber.

In certain embodiments, the sample chamber comprises one first (or inlet) well, two second (or imaging) wells, and two third (or outlet) wells.

In certain embodiments, the sample chamber comprises one first (or inlet) well, four second (or imaging) wells, and four third (or outlet) wells.

In certain embodiments of the multi-well plate, the mixing well is configured to have a volume of about 1 µL to about 500 µL (e.g., about 1 µL to about 300 µL, about 1 µL to about 200 µL, about 1 µL to about 100 µL, about 1 µL to about 50 µL, about 1 µL to about 20 µL, about 1 µL to about 10 µL, about 10 µL to about 500 µL, about 50 µL to about 500 µL, about 100 µL to about 500 µL, about 10 µL to about 50 µL, about 50 µL to about 100 µL, about 20 µL to about 100 µL, about 50 µL to about 200 µL).

In certain embodiments of the multi-well plate, the sample chamber is configured to have a volume of about 1 µL to about 500 µL (e.g., about 1 µL to about 300 µL, about 1 µL to about 200 µL, about 1 µL to about 100 µL, about 1 µL to about 50 µL, about 1 µL to about 20 µL, about 1 µL to about 10 µL, about 10 µL to about 500 µL, about 50 µL to about 500 µL, about 100 µL to about 500 µL, about 10 µL to about 50 µL, about 50 µL to about 100 µL, about 20 µL to about 100 µL, about 50 µL to about 200 µL).

In certain embodiments of the multi-well plate, the imaging chamber is configured to have a volume of about 0.2 µL to about 10 µL (e.g., about 0.2 µL to about 5 µL, about 0.2 µL to about 2 µL, about 0.2 µL to about 1 µL, about 0.2 µL to about 0.5 µL, about 0.5 µL to about 10 µL, about 1 µL to about 10 µL, about 2 µL to about 10 µL, about 5 µL to about 10 µL, about 0.5 µL to about 2 µL, about 2 µL to about 5 µL).

In certain embodiments of the multi-well plate, the imaging chamber has a top wall (ceiling) and a bottom wall (floor) with a uniform height (or depth) therebetween.

In certain embodiments of the multi-well plate, the imaging chamber has a top wall (ceiling) and a bottom wall (floor) with a non-uniform height (or depth) therebetween.

In certain embodiments of the multi-well plate, the imaging chamber comprises a first portion of the top wall (ceiling) and a first portion of the bottom wall (floor) providing a first height (or depth) therebetween and a second portion of the top wall (ceiling) and a second portion of the bottom wall (floor) providing a second height (or depth) therebetween.

The height(s) of the imaging chamber of the multi-well plate can be any suitable value, for example, in the range from about 1 µm to about 1 mm (e.g., about 1 µm to about 0.5 mm, about 1 µm to about 0.1 mm, about 1 µm to about 50 µm, about 1 µm to about 20 µm, about 1 µm to about 10 µm, about 5 µm to about 1 mm, about 10 µm to about 1 mm, about 0.1 mm to about 1 mm, about 0.5 mm to about 1 mm, about 2 µm to about 10 µm, about 10 µm to about 0.1 mm).

In certain embodiments, the height(s) is in the range from about 1 µm to about 20 µm (e.g., about 1 µm to about 5 µm, about 5 µm to about 10 µm, about 10 µm to about 15 µm, about 15 µm to about 20 µm). In certain embodiments, the height(s) is in the range from about 20 µm to about 1 mm (e.g., about 20 µm to about 0.1 mm, about 0.1 mm to about 0.5 mm, about 0.5 mm to about 1 mm).

In certain embodiments of the imaging chamber, the top wall (ceiling) and/or the bottom wall (floor) has one or more markings, e.g., as a counting grid, for reference or for autofocusing.

In certain embodiments, the one or more markings has unit markings ranging from about 0.1 µm to about 1 mm (e.g., about 0.1 µm to about 1 mm, about 1 µm to about 1 mm, about 10 µm to about 1 mm, about 0.1 mm to about 1 mm, about 0.1 µm to about 0.1 mm, about 0.1 µm to about 10 µm, about 0.1 µm to about 1 µm, about 1 µm to about 10 µm, about 1 µm to about 25 µm, about 10 µm to about 0.1 mm).

In certain embodiments, the one or more markings has unit markings ranging from about 1 µm to about 25 µm (e.g., about 1 µm to about 5 µm, about 5 µm to about 10 µm, about 10 µm to about 25 µm).

In certain embodiments of the multi-well plate, the first (or inlet) well is open to ambient atmosphere (e.g., ambient pressure) during operation.

In certain embodiments of the multi-well plate, the first (or inlet) well is closed to ambient atmosphere (e.g., ambient pressure) during operation.

In certain embodiments of the multi-well plate, the third (or outlet) well is open to ambient atmosphere (e.g., ambient pressure) during operation.

In certain embodiments of the multi-well plate, the third (or outlet) well is closed to ambient atmosphere (e.g., ambient pressure) during operation.

In certain embodiments of the multi-well plate, the mixing well has on its bottom a staining agent in dry form.

In yet another aspect, the invention generally relates to a system for analyzing biological samples, wherein the system includes a multi-well plate disclosed herein.

In certain embodiments, the system further includes: at least one fluorescent light source; at least one bright-field light source; at least one optical system for light beam narrowing of the fluorescent light beam and/or the bright-field light beam; a detection device; and a computing unit.

In certain embodiments, the system includes two or more fluorescent light sources.

In certain embodiments, the system includes two or more bright-field light sources.

In yet another aspect, the invention generally relates to a method for preparing and analyzing samples. The method includes: preparing a liquid sample for analysis in the mixing well of a multi-well plate disclosed herein; introducing the prepared liquid sample into the first (or inlet) well of the sample chamber, whereby the liquid sample flows to fill up the image chamber of the second (or image) well and to the third (or outlet) well of the sample chamber; and analyzing the liquid sample via the optically transparent window of the second (or image) well.

In certain embodiments, the liquid sample has cells selected from red blood cells, bacteria, yeast, platelets, stem cells, islet cell, algae, primary cells (PBMCs, splenocytes, leukapheresis, apheresis, thymocytes), splenocytes, apheresis sample, and cancer cells (NCI-60 cell lines), Chinese hamster ovary (CHO) and Jurkat cells.

In certain embodiments of the method, preparing a liquid sample for analysis comprises mixing a sample with a staining agent (including dye or label).

In certain embodiments of the method, the staining agent is selected from Acridine Orange, Propidium Iodide, DAPI, Hoechst, 7AAD, Sytox Green, Sytox Red, DRAQ5/7, nuclear green/red/blue/far red, trypan blue, GFP, RFP, mCherry, BFP, mCardinal, YFP, CFP, Annexin V-FITC, -PE and PI, Caspase 3/7 and allophycocyanin (APC).

In certain embodiments of the method, analyzing the liquid sample comprises obtaining fluorescent and/or bright-field images of the liquid sample.

In certain embodiments of the method, analyzing the liquid sample includes obtaining fluorescent images of the liquid sample using two or more fluorescent light sources.

In certain embodiments of the method, analyzing the liquid sample includes obtaining bright-field images of the liquid sample using two or more bright-field light sources.

In certain embodiments, the method includes performing the sample preparation, introduction and/or analysis simultaneously on 2 or more (e.g., 4, 8, 16 or more) samples. In certain embodiments, the method includes performing the sample preparation, introduction and/or analysis simultaneously on 24 or more (e.g., 32, 48, 64 or more) samples. In certain embodiments, the method includes performing the sample preparation, introduction and/or analysis simultaneously on 96 or more samples. In certain embodiments, the method includes performing the sample preparation, introduction and/or analysis simultaneously on 384 or more samples.

In certain embodiments of the method, analyzing the liquid sample includes obtaining one or more of count number, concentration, size, morphology, transduction efficiency, apoptosis, viability, cell cycle, surface marker of a cell population and/or cell population ratio in the liquid sample.

In certain embodiments of the method, analyzing the liquid sample comprises obtaining a percentage or fraction of a fluorescently label cell population in the liquid sample.

In certain embodiments of the method, the liquid sample introduced into the first (or inlet) well of the sample chamber has a volume between about 20 µL to about 300 µL (e.g., about 20 µL to about 100 about 20 µL to about 50 about 30 µL to about 300 about 50 µL to about 300 about 100 µL to about 300 about 50 µL to about 100 µL).

In certain embodiments of the method, the liquid sample introduced into the first (or inlet) well of the sample chamber has a volume between about 50 µL to about 200 µL (e.g., about 50 µL to about 100 about 100 µL to about 150 about 150 µL to about 200 µL).

In yet another aspect, the invention generally relates to a sample chamber. The sample chamber includes an inlet for introducing the liquid sample for analysis, an imaging well, and an outlet for air escape or outflow of the liquid sample. The imaging well includes an imaging chamber for holding the liquid sample for observation or analysis wherein the imaging chamber is in fluid communication with the inlet; and an optically transparent window suitable for observation or analysis of the liquid sample inside the imaging chamber. The imaging chamber is characterized by a uniform height traversing at least a portion of the optically transparent window. The outlet is in fluid communication with the imaging chamber.

In certain embodiments of the sample chamber, the imaging chamber is configured to have a volume of about 0.2 µL to about 10 µL (e.g., about 0.2 µL to about 5 about 0.2 µL to about 2 µL, about 0.2 µL to about 1 µL, about 0.2 µL to about 0.5 µL, about 0.5 µL to about 10 µL, about 1 µL to about 10 µL, about 2 µL to about 10 µL, about 5 µL to about 10 µL, about 0.5 µL to about 2 µL, about 2 µL to about 5 µL).

In certain embodiments of the sample chamber, the imaging chamber comprises a top wall and a bottom wall with a uniform height (or depth) therebetween. In certain embodiments of the sample chamber, the imaging chamber comprises a top wall and a bottom wall with a non-uniform height (or depth) therebetween.

In certain embodiments, the imaging chamber includes a first portion of the top wall and a first portion of the bottom wall providing a first height (or depth) therebetween and a second portion of the top wall and a second portion of the bottom wall providing a second height (or depth) therebetween. In certain embodiments of the sample chamber, the height(s) is in the range from about 1 µm to about 1 mm (e.g., about 1 µm to about 0.5 mm, about 1 µm to about 0.1 mm, about 1 µm to about 50 µm, about 1 µm to about 20 µm, about 1 µm to about 10 µm, about 5 µm to about 1 mm, about 10 µm to about 1 mm, about 0.1 mm to about 1 mm, about 0.5 mm to about 1 mm, about 2 µm to about 10 µm, about 10 µm to about 0.1 mm).

In certain embodiments of the sample chamber, the height(s) is in the range from about 1 µm to about 20 µm (e.g., about 1 µm to about 5 µm, about 5 µm to about 10 µm, about 10 µm to about 15 µm, about 15 µm to about 20 µm).

In certain embodiments, the height(s) is in the range from about 20 µm to about 1 mm (e.g., about 20 µm to about 0.1 mm, about 0.1 mm to about 0.5 mm, about 0.5 mm to about 1 mm). In certain embodiments of the sample chamber, the height(s) is in the range from about 20 µm to about 1 mm (e.g., about 20 µm to about 0.1 mm, about 0.1 mm to about 0.5 mm, about 0.5 mm to about 1 mm).

In certain embodiments of the sample chamber, the top wall (ceiling) and/or the bottom wall (floor) of the imaging chamber has one or more markings, e.g., as a counting grid, for reference or for autofocusing.

In certain embodiments, the one or more markings has unit markings ranging from about 0.1 µm to about 1 mm (e.g., about 0.1 µm to about 1 mm, about 1 µm to about 1 mm, about 10 µm to about 1 mm, about 0.1 mm to about 1 mm, about 0.1 µm to about 0.1 mm, about 0.1 µm to about 10 µm, about 0.1 µm to about 1 µm, about 1 µm to about 10 µm, about 1 µm to about 25 µm, about 10 µm to about 0.1 mm).

In certain embodiments, the one or more markings has unit markings ranging from about 1 µm to about 25 µm (e.g., about 1 µm to about 5 µm, about 5 µm to about 10 µm, about 10 µm to about 25 µm).

In certain embodiments of the sample chamber, the inlet is open to ambient atmosphere (e.g., ambient pressure) during operation.

In certain embodiments of the sample chamber, the inlet is closed to ambient atmosphere (e.g., ambient pressure) during operation.

In certain embodiments of the sample chamber, the outlet is open to ambient atmosphere (e.g., ambient pressure) during operation.

In certain embodiments of the sample chamber, the outlet is closed to ambient atmosphere (e.g., ambient pressure) during operation.

In yet another aspect, the invention generally relates to a sample analysis unit, a multi-well plate, or a device that includes a sample chamber disclosed herein.

In yet another aspect, the invention generally relates to a method for preparing and analyzing samples. The method includes: introducing a liquid sample into an inlet of a sample chamber disclosed herein, whereby the liquid sample flows to fill up the image chamber and to the outlet of the sample chamber; and analyzing the liquid sample via the optically transparent window of the image chamber.

In certain embodiments, the method further includes preparing a liquid sample for analysis prior to introducing the liquid sample into the inlet of the sample chamber.

In yet another aspect, the invention generally relates to a system for analyzing biological samples, wherein the system includes a sample chamber disclosed herein.

In certain embodiments, the system includes: at least one fluorescent light source; at least one bright-field light source; at least one optical system for light beam narrowing of the fluorescent light beam and/or the bright-field light beam; a detection device; and a computing unit.

In certain embodiments, the system includes two or more fluorescent light sources. In certain embodiments, the system includes two or more bright-field light sources.

The following examples are meant to be illustrative of the practice of the invention and not limiting in any way.

EXAMPLES

An exemplary system has been constructed and used to demonstrate counting of CHO cells stained with trypan blue, PBMCs stained with AOPI, and Jurkat cells stained with AOPI. There are used to demonstrate the cell counting, cell size and viability measurements and capabilities of the exemplary system.

CHO Cell Counting with Manual Pipetting

Figure 8A:
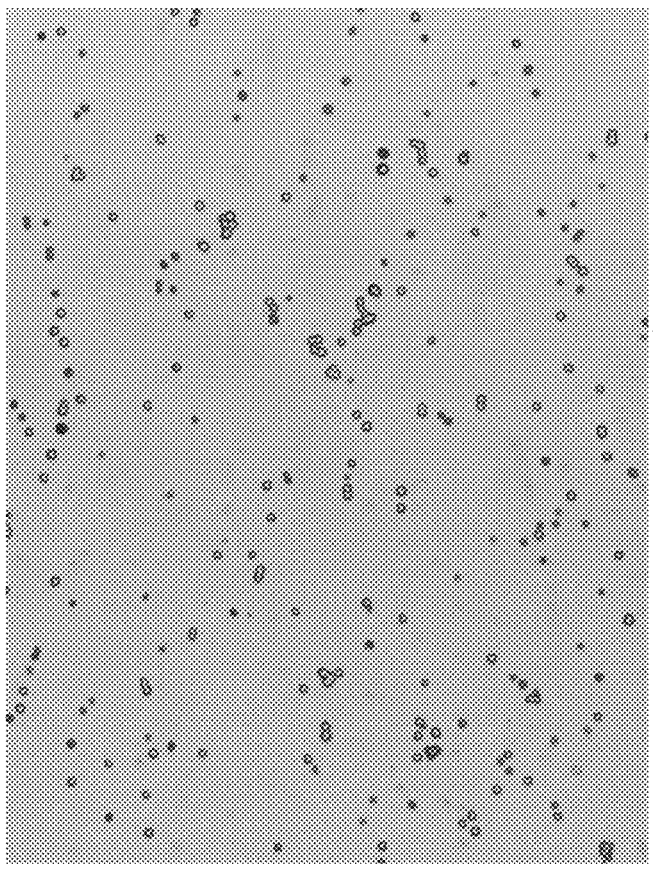
Figure 8A:
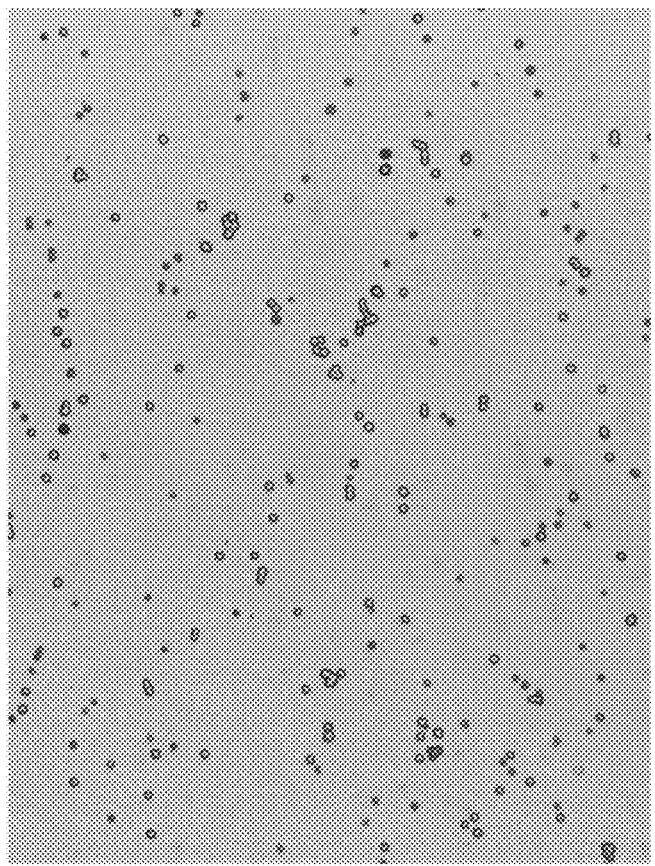

CHO cells were cultured in CD CHO Medium (Gibco) supplemented with 1× Glutamax and 1× HT supplement at 37° C. and 5% $CO_2$. The CHO cells were collected from the flask and poured into a disposable trough. Using a multichannel pipette (12-channels), 50 µL of CHO cells were pipetted into the sample introduction ports of the cell counting plate. Repeat process to fill all 24 counting chambers. The exemplary system is then used to image using bright field at each counting chamber and directly count the number of CHO cells which is then automatically converted and output cell concentrations as the results, as well as cell size (FIGS. 8A and 8B)

CHO Cell Counting and Viability Measurement Using Trypan Blue with Manual Pipetting CHO cells were cultured in CD CHO Medium (Gibco) supplemented with 1× Glutamax and 1× HT supplement at 37° C. and 5% $CO_2$. The CHO cells were collected from the flask and poured into a disposable trough. Using a multi-channel pipette (12-channels), 50 µL of CHO cells were pipetted into the mixing wells of the cell counting plate. Next, trypan blue stains were also pipetted into the mixing wells to have a 1:1 ratio with the cells. Pipette 50 µL of the stained CHO cells into the sample introduction ports. Repeat process to fill all 24 counting chambers. The exemplary system is then used to image using bright field at each counting chamber and directly count the number of live CHO cells and dead CHO cells, which is then automatically converted and output cell concentrations, cell sizes, and viability as the results. (FIGS. 9A and 9B).

PBMC Counting and Viability Measurement Using AOPI with Liquid Handler

Figure 10A:
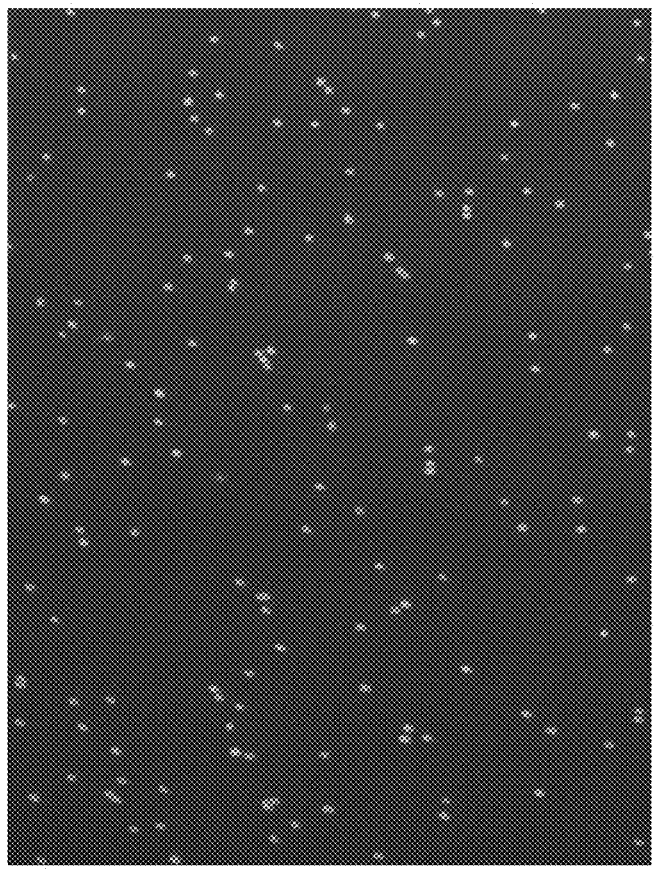
Figure 10A:
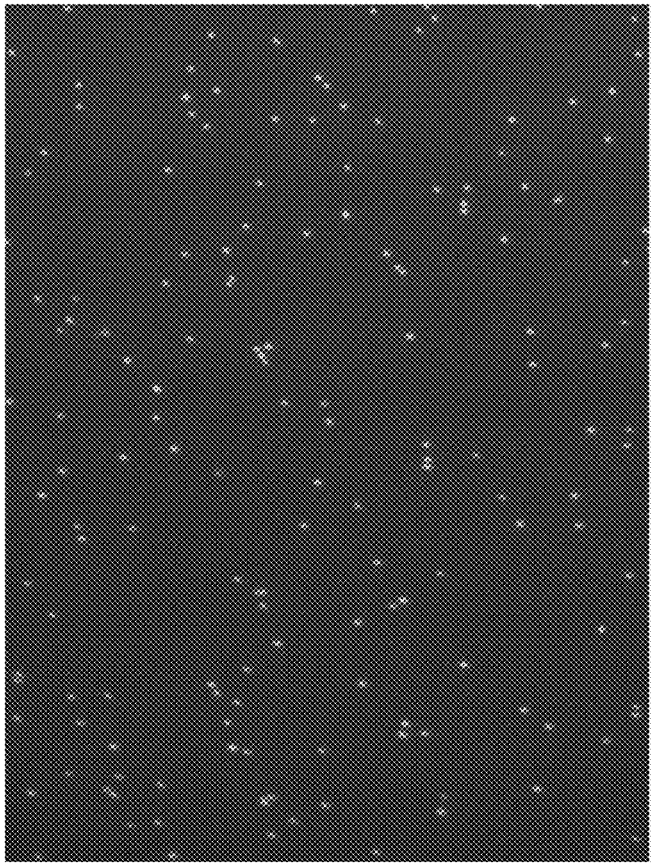
Figure 10B:
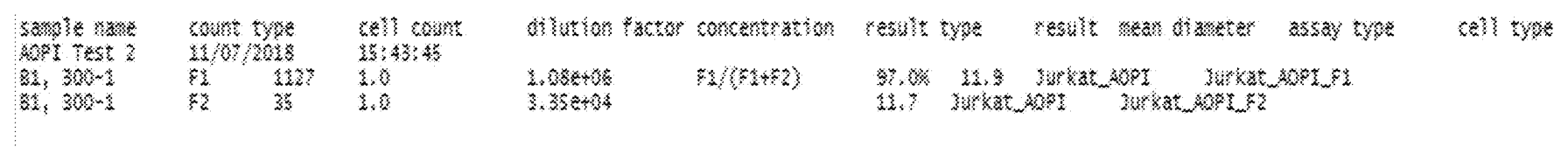

PBMCs were collected patients and poured into a disposable trough. Using a liquid handler, 50 µL of PBMCs were mixed in a trough with 50 µL of AOPI. Next, the liquid handler aspirated 50 µL of the stained PBMCs and pipetted into the sample introduction ports. Repeat process to fill all 24 counting chambers. The exemplary system is then used to image using bright field and green/red fluorescence at each counting chamber and directly count the number of live and dead PBMCs which is then automatically converted and output cell concentrations, cell sizes and viability as the results. (FIGS. 10A and 10B).

Jurkat Cell Counting and Viability Measurement Using AOPI with Liquid Handler

Figure 11A:
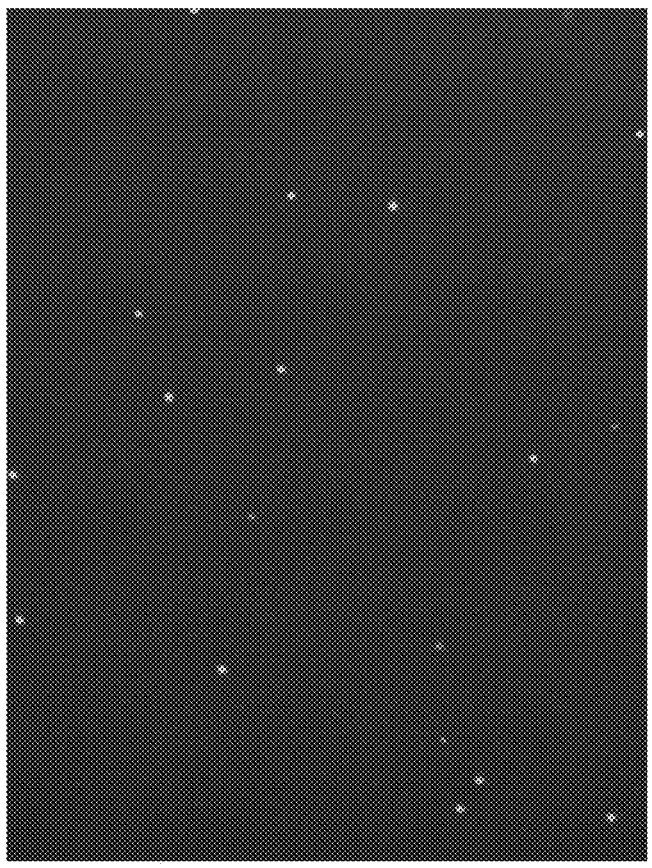
Figure 11A:
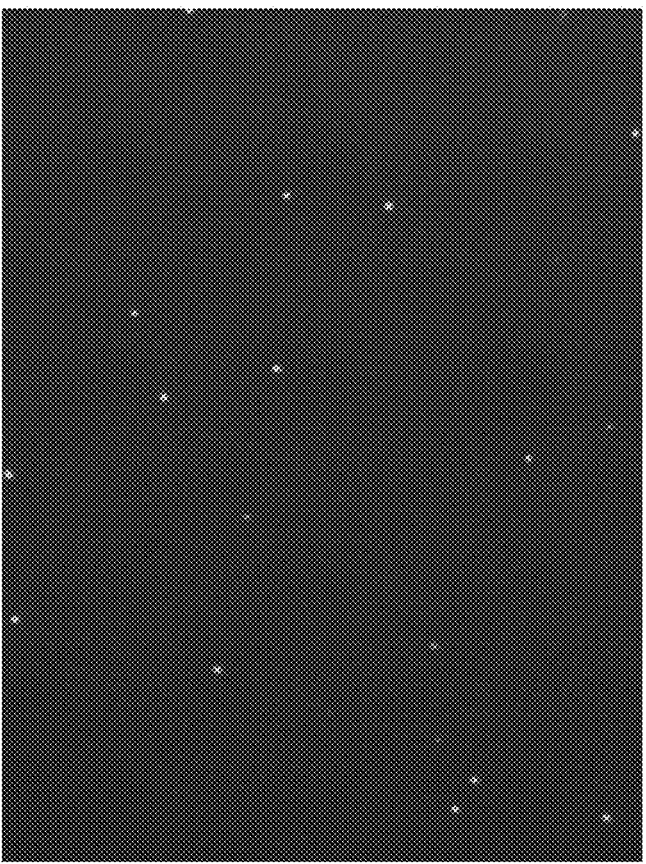

Jurkat cells were cultured in RPMI (Gibco) supplemented with 10% FBS and 1% Pen/Strept at 37° C. and 5% $CO_2$. The Jurkat cells were collected and aspirated by a liquid handler. Using a liquid handler, 50 µL of Jurkat cells were mixed in the mixing well on the cell counting plate with 50 µL of AOPI. Next, the liquid handler aspirated 50 µL of the stained Jurkat cells and pipetted into the sample introduction ports. Repeat process to fill all 24 counting chambers. The exemplary system is then used to image using bright field and green/red fluorescence at each counting chamber and directly count the number of live and dead Jurkat cells which is then automatically converted and output cell concentrations, sizes and viability as the results. (FIGS. 11A and 11B).

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A sample analysis unit, comprising:
 (a) a mixing well for preparation of a liquid sample for analysis; and
 (b) a sample chamber deposed in spatial proximity to the mixing well without fluid communication therebetween, comprising:
  (i) an inlet for introducing the liquid sample for analysis to the sample chamber;
  (ii) an imaging well comprising
   an imaging chamber for holding the liquid sample for observation or analysis wherein the imaging chamber is in fluid communication with the inlet;
   an optically transparent window suitable for observation or analysis of the liquid sample inside the imaging chamber,
 wherein the imaging chamber is characterized by a uniform height traversing at least a portion of the optically transparent window; and (iii) an outlet for air escape or outflow of the liquid sample, wherein the outlet is in fluid communication with the imaging chamber, wherein the mixing well and the sample chamber together form the sample analysis unit.

2. The sample analysis unit of claim 1, wherein the sample chamber comprises:
(ii) two or more imaging wells, each comprising
an imaging chamber for holding the liquid sample for observation or analysis wherein said imaging chamber is in fluid communication with the inlet;
an optically transparent window suitable for observation or analysis of the liquid sample inside said imaging chamber,
wherein said imaging chamber is characterized by a uniform height traversing at least a portion of the optically transparent window; and
(iii) two or more of corresponding outlets for air escape or outflow of the liquid sample, each being in fluid communication with a corresponding imaging chamber.

3. The sample analysis unit of claim 1, wherein the sample chamber comprises one inlet, two imaging wells, and two outlets.

4. The sample analysis unit of claim 1, wherein the sample chamber comprises one inlet, four imaging wells, and four outlets.

5. The sample analysis unit of claim 1, wherein the mixing well is configured to have a volume of about 1 μL to about 500 μL.

6. The sample analysis unit of claim 5, wherein the sample chamber is configured to have a volume of about 1 μL to about 500 μL.

7. The sample analysis unit of claim 6, wherein the imaging chamber is configured to have a volume of about 0.2 μL to about 10 μL.

8. The sample analysis unit of claim 1, wherein the imaging chamber comprises a top wall and a bottom wall with a uniform height (or depth) therebetween.

9. The sample analysis unit of claim 1, wherein the imaging chamber comprises a top wall and a bottom wall with a non-uniform height (or depth) therebetween.

10. The sample analysis unit of claim 1, wherein the imaging chamber comprises a first portion of the top wall and a first portion of the bottom wall providing a first height (or depth) therebeween and a second portion of the top wall and a second portion of the bottom wall providing a second height (or depth) therebetween.

11. The sample analysis unit of claim 8, wherein the height(s) is in the range from about 1 μm to about 1 mm.

12. The sample analysis unit of claim 1, wherein the top wall and/or the bottom of the imaging chamber wall comprises one or more markings for counting grid, reference or autofocus.

13. The sample analysis unit of claim 1, wherein the inlet is open to ambient atmosphere or pressure during operation.

14. The sample analysis unit of claim 1, wherein the outlet is open to ambient atmosphere or pressure during operation.

15. The sample analysis unit of claim 1, wherein the mixing well comprises a bottom on which a staining agent in dry form is provided.

16. A multi-well plate or device comprising a sample analysis unit of claim 1.

17. A multi-well plate for sample preparation and analysis, comprising:
(a) a mixing well for preparation of a liquid sample for analysis; and (b) a sample chamber deposed in spatial proximity to the mixing well without fluid communication therebetween, comprising:
(i) a first (or inlet) well for introducing the liquid sample for analysis to the sample chamber;
(ii) a second (or imaging) well comprising
an imaging chamber for holding the liquid sample for observation or analysis wherein the imaging chamber is in fluid communication with the first (or inlet well);
an optically transparent window suitable for observation or analysis of the liquid sample inside the imaging chamber,
wherein the imaging chamber is characterized by a uniform height traversing at least a portion of the optically transparent window; and
(iii) a third (or outlet) well for air escape or outflow of the liquid sample, wherein the third (or outlet) well is in fluid communication with the imaging chamber,
wherein the mixing well and the sample chamber together form a unit of the multi-well plate.

18. The multi-well plate of claim 17, comprising 2 or more of the multi-well units.

19. The multi-well plate of claim 17, comprising 96 or more of the multi-well units.

20. The multi-well plate of claim 17, comprising 384 or more of the multi-well units.

21. A system for analyzing biological samples, comprising a sample analysis unit or a multi-well plate of claim 1.

22. The system of claim 21, further comprising:
at least one fluorescent light source;
at least one bright-field light source;
at least one optical system for light beam narrowing of the fluorescent light beam and/or the bright-field light beam;
a detection device; and
a computing unit.

23. The system of claim 22, comprising two or more fluorescent light sources.

24. The system of claim 21, comprising two or more bright-field light sources.

25. A method for preparing and analyzing samples, comprising:
preparing a liquid sample for analysis in the mixing well of claim 1;
introducing the prepared liquid sample into the first (or inlet) well of the sample chamber, whereby the liquid sample flows to fill up the image chamber of the second (or image) well and to the third (or outlet) well of the sample chamber; and
analyzing the liquid sample via the optically transparent window of the second (or image) well.

26. A sample chamber, comprising:
an inlet for introducing the liquid sample for analysis;
an imaging well comprising
an imaging chamber for holding the liquid sample for observation or analysis wherein the imaging chamber is in fluid communication with the inlet;
an optically transparent window suitable for observation or analysis of the liquid sample inside the imaging chamber,
wherein the imaging chamber is characterized by a uniform height traversing at least a portion of the optically transparent window; and
an outlet for air escape or outflow of the liquid sample, wherein the outlet is in fluid communication with the imaging chamber.

27. A sample analysis unit, a multi-well plate, or a device comprising a sample chamber of claim 26.

28. A method for preparing and analyzing samples, comprising:
- introducing a liquid sample into an inlet of a sample chamber according to claim 26, whereby the liquid sample flows to fill up the image chamber and to the outlet of the sample chamber; and
- analyzing the liquid sample via the optically transparent window of the image chamber.

29. A system for analyzing biological samples, comprising a sample chamber according to claim 26.

* * * * *